(12) United States Patent
Gray et al.

(10) Patent No.: US 11,155,623 B2
(45) Date of Patent: Oct. 26, 2021

(54) ANTIBODY THERAPEUTICS THAT BIND CTLA4

(71) Applicant: Sorrento Therapeutics, Inc., San Diego, CA (US)

(72) Inventors: John Dixon Gray, San Diego, CA (US); Heyue Zhou, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 401 days.

(21) Appl. No.: 16/243,016

(22) Filed: Jan. 8, 2019

(65) Prior Publication Data

US 2019/0127469 A1    May 2, 2019

Related U.S. Application Data

(63) Continuation of application No. 15/043,157, filed on Feb. 12, 2016, now Pat. No. 10,202,453.

(60) Provisional application No. 62/116,353, filed on Feb. 13, 2015.

(51) Int. Cl.
   *C07K 16/28* (2006.01)
   *A61K 39/395* (2006.01)

(52) U.S. Cl.
   CPC ...... *C07K 16/2818* (2013.01); *C07K 2317/21* (2013.01); *C07K 2317/33* (2013.01); *C07K 2317/56* (2013.01); *C07K 2317/70* (2013.01); *C07K 2317/76* (2013.01); *C07K 2317/92* (2013.01)

(58) Field of Classification Search
   None
   See application file for complete search history.

(56) References Cited

U.S. PATENT DOCUMENTS

| | | | |
|---|---|---|---|
| 6,632,927 B2 | 10/2003 | Adair et al. | |
| 7,311,910 B2 * | 12/2007 | Linsley | C07K 14/70521 424/130.1 |
| 10,202,453 B2 * | 2/2019 | Gray | C07K 16/2818 |
| 2005/0049402 A1 | 3/2005 | Babcook et al. | |
| 2011/0081354 A1 | 4/2011 | Korman et al. | |
| 2016/0237154 A1 * | 8/2016 | Gray | A61P 37/06 |
| 2017/0233476 A1 * | 8/2017 | Zhou | C07K 16/2818 424/173.1 |

FOREIGN PATENT DOCUMENTS

| | | |
|---|---|---|
| EP | 1792991 A1 | 6/2007 |
| JP | 2002537226 A | 11/2002 |
| JP | 2004512005 A | 4/2004 |
| WO | 00/37504 A2 | 6/2000 |
| WO | WO 00/37504 | 6/2000 |
| WO | WO 2001/014424 | 3/2001 |
| WO | 2009/100140 A1 | 8/2009 |
| WO | WO-2016130898 A2 * | 8/2016 ............. A61P 25/28 |
| WO | WO-2016130986 A1 * | 8/2016 ............. A61P 35/00 |

OTHER PUBLICATIONS

D Schönfeld et al., "An Engineered Lipocalin Specific for CTLA-4 Reveals a Combining Site With Structural and Conformational Features Similar to Antibodies," Proc Natl Acad Sci, 106(20): 8198-8203(May 2009).
International Preliminary Report on Patentability for PCT/US2016/017713, published Aug. 15, 2017, 8 pages.
International Preliminary Report on Patentability for PCT/US2016/017859, published Aug. 15, 2017, 5 pages.
International Search Report for PCT/US2016/017713, published Sep. 1, 2016, 6 pages.
International Search Report for PCT/US2016/017859, published May 19, 2016, 3 pages.
Panka et al., 1988, Proc. Natl. Acad. Sci. USA, 85: 3080-3084.
PCT/ISA/206—Invitation to Pay Additional Fees and, where applicable, Protest Fee for PCT/US2016/017713, 3 pages.
Ribas, et al., "Tremelimumab (CP-675,206), a cytotoxic T lymphocyte associated antigen 4 blocking monoclonal antibody in clinical development for patients with cancer." The Oncologist—Jul. 2007, (7:873-83).
Rudikoff et al. 1982, Proc. Natl. Acad. Sci. USA, 79: 1979-1983.
Supplementary Partial European Search Report relating to corresponding application EP 16749944, completed on May 30, 2018 dated Jun. 13, 2018.

* cited by examiner

*Primary Examiner* — Ilia I Ouspenski
(74) *Attorney, Agent, or Firm* — McNeill Baur PLLC

(57) ABSTRACT

There is disclosed compositions and methods relating to or derived from anti-CTLA4 antibodies. More specifically, there is disclosed fully human antibodies that bind CTLA4, CTLA4-antibody binding fragments and derivatives of such antibodies, and CTLA4-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease requiring either stimulation of immune responses or suppression. Stimulation is achieved using antibodies that block binding of human CTLA4 to human B7 and diseases amenable to treatment by stimulation and augmentation of prolonging of immune responses include cancers of the prostate, kidney, colon, lung or breast; pathogenic infections; diseases associated with the CNS e.g. amyloidogenic diseases including Alzheimer's disease; and diseases with inflammatory or allergic components. Diseases amenable to treatment include graft versus host disease, host versus graft disease, allergy, autoimmune diseases and other inflammatory diseases.

8 Claims, 6 Drawing Sheets
Specification includes a Sequence Listing.

SEQUENCE LISTING

<160> NUMBER OF SEQ ID NOS: 46

<210> SEQ ID NO 1
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Glu Val Gln Leu Val Gln Ser Gly Gly Gly Leu Val Gln Pro Gly Arg
1               5                   10                  15

Ser Leu Arg Leu Ser Cys Arg Gly Ser Asn Phe Asn Phe Asp Asp Leu
            20                  25                  30

Ala Ile Ser Trp Val Arg Gln Ala Pro Gly Lys Gly Leu Glu Trp Leu
        35                  40                  45

Gly Phe Val Arg Ser Lys Ala Tyr Gly Glu Thr Thr Asp Tyr Val Ala
    50                  55                  60

Ser Val Lys Gly Arg Phe Thr Ile Ser Arg Asp Asp Ser Lys Phe Ile
65                  70                  75                  80

Ala Trp Leu Gln Met Asp Ser Leu Lys Thr Asp Asp Thr Ala Val Tyr
                85                  90                  95

Tyr Cys Thr Thr Phe Asn Tyr Trp Gly Gln Gly Thr Leu Val Thr Val
                100                 105                 110

Ser Ser
```

```
<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Leu Pro Val Leu Thr Gln Pro Pro Ser Val Ser Val Ala Pro Gly Lys
1               5                   10                  15

Thr Ala Arg Ile Ser Cys Gly Gly Asn Asn Ile Ala Ser Glu Ala Val
            20                  25                  30

His Trp Tyr Gln Lys Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Arg Ile Ser Arg Val Asp Ala Gly
65                  70                  75                  80

Asp Glu Ala Asp Tyr Tyr Cys Gln Val Trp Asp Arg Thr Thr Asp Gln
                85                  90                  95

Pro Val Phe Gly Gly Gly Thr Lys Leu Thr Val Leu
            100                 105

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Met Gln Leu Val Gln Ser Gly Ala Glu Val Lys Met Pro Gly Ser
1               5                   10                  15

Ser Val Arg Ile Ser Cys Lys Ala Ser Gly Gly Ser Phe Thr Thr His
            20                  25                  30

Phe Ile Asn Trp Val Arg Gln Ala Pro Gly Gln Gly Leu Glu Trp Met
        35                  40                  45

Gly Trp Met Asn Pro Asn Thr Gly Asn Thr Gly Tyr Ala Glu Arg Phe
    50                  55                  60

Gln Gly Arg Val Thr Leu Thr Arg Asp Thr Ser Ile Ser Thr Ala Tyr
65                  70                  75                  80

Leu Glu Leu Ser Ser Leu Arg Ser Asp Asp Thr Ala Val Tyr Tyr Cys
                85                  90                  95

Ala Arg Asn Pro Ala Glu Ser Gly Arg Phe Asp Pro Trp Gly Gln Gly
            100                 105                 110

Thr Leu Val Thr Val Ser Ser
        115

<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ser Ala Leu Thr Gln Pro Pro Ser Ala Ser Gly Ser Pro Gly Arg
1               5                   10                  15
```

Ser Val Thr Ile Ser Cys Thr Gly Thr Ser Asn Asn Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Gly Thr Trp Asp Gly Ser
                85                  90                  95

Leu Asn Ala Tyr Val Phe Gly Thr Gly Thr Lys Val Thr Val Leu
            100                 105                 110

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Val Ser Asn Asn
            20                  25                  30

Tyr Met Asn Trp Val Arg Gln Ala Pro Gly Lys Gly Leu Glu Trp Val
        35                  40                  45

Ser Val Ile Tyr Arg Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
65                  70                  75                  80

Gln Met Asn Ser Leu Arg Thr Glu Asp Thr Ala Val Tyr Tyr Cys Leu
                85                  90                  95

Arg Glu Gly Gly Thr Ser Gly Asp Tyr Val Asn Asp Trp Gly Gln Gly
            100                 105                 110

Thr Leu Val Thr Val Ser Ser
        115

<210> SEQ ID NO 6
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Lys Asn Arg Pro Ser Gly Val Pro Asp Arg Phe
 50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ala Tyr Asp Ser Ser
                85                  90                  95

Leu Ser Val Val Phe Gly Gly Gly Thr Lys Leu Thr Val Leu
            100                 105                 110

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Met Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ile Gly Ser Tyr Ser Ser Gly Trp Tyr Arg Ala Phe Asp
            100                 105                 110

Ile Trp Gly Gln Gly Thr Met Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Gln Leu Leu Ile
        35                  40                  45

Tyr Lys Ala Ser Asn Leu Gln Ser Gly Val Pro Ser Arg Phe Ser Gly
    50                  55                  60

Ser Gly Ser Val Thr Glu Phe Ser Leu Thr Ile Ser Ser Leu Leu Pro
65                  70                  75                  80

Glu Asp Phe Ala Thr Tyr Tyr Cys Gln Gln Tyr Ser Arg Pro Pro Trp
                85                  90                  95

Thr Phe Gly Gln Gly Thr Lys Val Glu Ile Lys
            100                 105

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Thr Pro Gly Lys Gly Leu Glu Trp Val
        35                  40                  45

Ser Val Asn Tyr Asn Asp Gly Phe Gly Thr Phe Asn Gly Tyr Tyr Ala
    50                  55                  60

Asp Ser Val Lys Gly Arg Phe Ile Ile Ser Arg Asp Asn Ser Lys Asn
65                  70                  75                  80

Thr Leu Tyr Leu Gln Met Asn Ser Leu Arg Val Asp Asp Thr Ala Val
                85                  90                  95

Tyr Tyr Cys Ala Arg Asp Ser Gly Val Ala Gly Pro Tyr Tyr Phe Asp
            100                 105                 110

Asn Trp Gly Gln Gly Thr Leu Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Ser Pro Leu
                85                  90                  95

Thr Phe Gly Gly Gly Thr Lys Leu Glu Ile Lys
            100                 105

<210> SEQ ID NO 11
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ala
1               5                   10                  15

Thr Val Lys Val Ser Cys Thr Ala Ser Gly Phe Pro Phe Arg Asn Tyr
            20                  25                  30

Ala Met His Trp Val Arg Gln Ala Pro Gly Gln Arg Leu Glu Trp Leu
         35                  40                  45

Gly Trp Ile Asp Ala Gly Asn Gly Asn Thr Lys Tyr Ser Gln Thr Phe
 50                  55                  60

His Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Leu Leu Trp Pro Tyr Leu Val Thr Ser Gly Gly Ala Phe
             100                 105                 110

Asp Ile Trp Gly Gln Gly Thr Met Val Thr Val Ser Ser
         115                 120                 125

<210> SEQ ID NO 12
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Tyr Glu Leu Met Gln Pro Pro Ser Thr Ser Gly Thr Pro Gly Gln
 1               5                  10                  15

Arg Val Thr Ile Ser Cys Ser Gly Ser Ser Ser Asn Ile Gly Ser His
                 20                  25                  30

Ile Val Asn Trp Tyr Gln Gln Phe Pro Gly Ala Ala Pro Gln Leu Leu
             35                  40                  45

Ile Tyr Asn Asp Asp Gln Arg Pro Ser Gly Val Pro Asp Arg Phe Ser
 50                  55                  60

Gly Ser Lys Ser Gly Ala Ser Ala Ser Leu Ala Ile Ser Gly Leu Gln
 65                  70                  75                  80

Ser Glu Asp Glu Ala His Tyr Tyr Cys Ser Ala Trp Asp Asp Ile Leu
                 85                  90                  95

Lys Gly Pro Val Phe Gly Gly Gly Thr Lys Leu Thr Val Leu
             100                 105                 110

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr His
                 20                  25                  30

Tyr Ile His Trp Val Arg Gln Ala Pro Gly Gln Gly Leu Glu Trp Met
             35                  40                  45

Ala Ile Ile Asn Pro Asn Asp Gly Val Lys Val Tyr Ala Gln Lys Phe
 50                  55                  60

Lys Gly Arg Leu Thr Val Ala Ser Asp Thr Ser Ala Thr Thr Val Tyr
 65                  70                  75                  80

Met Asp Leu Ser Gly Leu Thr Ser Asp Thr Ala Val Tyr Tyr Cys
                 85                  90                  95

Gly Arg Glu Gln His Gly Gly His Asp Tyr Trp Gly Gln Gly Thr
                100                 105                 110

Leu Val Thr Val Ser Ser
        115

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Lys Ser Tyr Thr Ser Ser
                85                  90                  95

Ser Thr Pro Tyr Val Phe Gly Thr Gly Thr Lys Val Thr Val Leu
            100                 105                 110

<210> SEQ ID NO 15
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Gln Ser Gly Gly Gly Leu Val Gln Pro Gly Arg
1               5                   10                  15

Ser Leu Arg Leu Ser Cys Arg Gly Ser Asn Phe Asn Phe Asp Asp Leu
            20                  25                  30

Ala Ile Ser Trp Val Arg Gln Ala Pro Gly Lys Gly Leu Glu Trp Leu
        35                  40                  45

Gly Phe Val Arg Ser Lys Ala Tyr Gly Glu Thr Thr Asp Tyr Val Ala
    50                  55                  60

Ser Val Lys Gly Arg Phe Thr Ile Ser Arg Asp Asp Ser Lys Phe Ile
65                  70                  75                  80

Ala Trp Leu Gln Met Asp Ser Leu Lys Thr Asp Asp Thr Ala Val Tyr
                85                  90                  95

Tyr Cys Thr Thr Phe Asn Tyr Trp Gly Gln Gly Thr Leu Val Thr Val
            100                 105                 110

Ser Ser

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 16

Leu Pro Val Leu Thr Gln Pro Pro Ser Val Ser Val Ala Pro Gly Lys
1               5                   10                  15

Thr Ala Arg Ile Ser Cys Gly Gly Asn Asn Ile Ala Ser Glu Ala Val
            20                  25                  30

His Trp Tyr Gln Lys Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Arg Ile Ser Arg Val Asp Ala Gly
65                  70                  75                  80

Asp Glu Ala Asp Tyr Tyr Cys Gln Val Trp Asp Arg Thr Thr Asp Gln
                85                  90                  95

Pro Val Phe Gly Gly Gly Thr Lys Leu Thr Val Leu
            100                 105

<210> SEQ ID NO 17
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Gly Tyr Gly Gly Tyr Phe Asp Tyr Trp Gly Gln Gly Thr
            100                 105                 110

Leu Val Thr Val Ser Ser
        115

<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Tyr Glu Leu Met Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Asp Trp Leu Gln Gln His Gln Gly His Pro Pro Lys Leu Leu
        35                  40                  45

```
Ser Tyr Arg Asn Asn Asp Arg Pro Ser Gly Ile Ser Glu Arg Phe Ser
    50                  55                  60

Ala Ser Arg Ser Gly Ser Thr Ala Ser Leu Thr Ile Thr Gly Leu Gln
65                  70                  75                  80

Pro Glu Asp Glu Ala Asp Tyr Tyr Cys Leu Ala Trp Asp Ser Ser Leu
                85                  90                  95

Ser Ala Trp Val Phe Gly Gly Gly Thr Lys Val Thr Val Leu
            100                 105                 110

<210> SEQ ID NO 19
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Met Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asn Ser
            20                  25                  30

Tyr Ile His Trp Val Arg Gln Ala Pro Gly Gln Gly Leu Glu Trp Val
        35                  40                  45

Gly Arg Leu Ile Pro Ser Ser Gly Tyr Thr Ile Phe Ser Gln Lys Leu
    50                  55                  60

Gln Gly Arg Val Ser Met Thr Arg Asp Thr Ser Met Ser Thr His Tyr
65                  70                  75                  80

Leu Thr Leu Ser His Leu Arg Pro Glu Asp Thr Ala Val Tyr Tyr Cys
                85                  90                  95

Ala Thr Asp Gly Gly Asn Tyr Asn Leu Asp Phe Trp Gly Gln Gly Thr
            100                 105                 110

Leu Val Thr Val Ser Ser
        115

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Pro Val Leu Thr Gln Pro Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Ser Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Pro Tyr Val Phe Gly Thr Gly Thr Lys Val Thr Val Leu
            100                 105                 110
```

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Thr Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Gly Ser Glu Asp Thr Ala Val Tyr Tyr Cys
                85                  90                  95

Ala Arg Glu Ser Gly Ser Tyr Leu Asp Pro Trp Gly Gln Gly Thr Leu
            100                 105                 110

Val Thr Val Ser Ser
        115

<210> SEQ ID NO 22
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Pro Asn Asn Lys Asn Tyr Leu Thr Trp Tyr Gln Gln Lys Pro Gly Gln
        35                  40                  45

Pro Pro Lys Leu Leu Met Tyr Trp Ala Ser Thr Arg Glu Ser Gly Val
    50                  55                  60

Pro Asp Arg Phe Ser Ala Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Arg Ser Gly Pro Tyr Thr Phe Gly Gln Gly Thr Lys Val Glu Ile
            100                 105                 110

Lys

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Phe Val Lys Pro Gly Arg
1               5                   10                  15

Ser Leu Arg Leu Ser Cys Thr Ala Ser Gly Phe Thr Phe Gly Asp Tyr
            20                  25                  30

Gly Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95

Tyr Cys Thr Arg Gly His Tyr Ser Ala Ser Ile Trp Gly Gln Gly Thr
            100                 105                 110

Leu Val Thr Val Ser Ser
        115

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Arg Pro Asp Gln Ala Pro Val Leu Val Ile Tyr
        35                  40                  45

Ser Asp Asn Asp Arg Pro Ser Gly Ile Pro Glu Arg Phe Ser Gly Ser
    50                  55                  60

Ser Ser Gly His Thr Ala Thr Leu Thr Ile Ser Arg Val Glu Ala Gly
65                  70                  75                  80

Asp Glu Ala Asp Tyr Phe Cys Gln Val Trp Asp Ser Asn Lys Asn Glu
                85                  90                  95

Trp Val Phe Gly Gly Gly Thr Lys Leu Thr Val Leu
            100                 105

<210> SEQ ID NO 25
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Asp Gly His
            20                  25                  30

Tyr Met His Trp Val Arg Gln Ala Pro Gly Gln Arg Leu Glu Trp Met
        35                  40                  45

Gly Trp Val Asp Pro His Ser Gly Ala Thr Asn Tyr Ala Gln Asn Phe

```
                    50                  55                  60
Gln Gly Gly Val Thr Met Thr Arg Asp Thr Ser Ile Asn Thr Val Tyr
 65                  70                  75                  80

Met Glu Leu Ser Ser Leu Lys Ser Asp Thr Ala Val Tyr Tyr Cys
                 85                  90                  95

Ala Arg Asp Phe Tyr Asp Ser Ala Lys Ser Gly Ala Phe Asp Ile
                100                 105                 110

Trp Gly Gln Gly Thr Met Val Thr Val Ser Ser
            115                 120

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Ile Gln Leu Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Asn Ser Phe Pro Trp
                 85                  90                  95

Ala Phe Gly Gln Gly Thr Lys Val Glu Ile Lys
                100                 105

<210> SEQ ID NO 27
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ala
  1               5                  10                  15

Ser Val Lys Val Ser Cys Lys Thr Ser Gly Asn Thr Phe Thr Asn Tyr
                 20                  25                  30

Tyr Met His Trp Val Arg Gln Ala Pro Gly Gln Gly Leu Glu Trp Met
             35                  40                  45

Gly Ile Met Asn Pro Ser Gly Ser Thr Ser Tyr Ala Gln Lys Phe
 50                  55                  60

Gln Gly Arg Val Thr Met Thr Arg Asp Lys Ser Thr Ser Thr Val Tyr
 65                  70                  75                  80

Met Glu Leu Ser Ser Leu Thr Ser Glu Asp Thr Ala Val Tyr Tyr Cys
                 85                  90                  95

Ala Arg Asp Leu Phe Pro His Ile Tyr Gly Asn Tyr Tyr Gly Met Asp
                100                 105                 110

Ile Trp Gly Gln Gly Thr Thr Val Thr Val Ser Ser
```

-continued

```
              115                 120
```

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Gln Ser Val Val Thr Gln Pro Pro Ser Val Ser Ala Ala Pro Gly Gln
1               5                   10                  15

Asn Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Arg Arg Ala Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Arg Ser Leu
                85                  90                  95

Thr Thr Asp Trp Val Phe Gly Gly Gly Thr Lys Leu Thr Val Leu
            100                 105                 110
```

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Ala
            20                  25                  30

Tyr Met Ser Trp Val Arg Gln Ala Pro Gly Lys Gly Leu Glu Trp Val
        35                  40                  45

Ser Val Ile Tyr Arg Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Arg
                85                  90                  95

Gly Glu Gly Gly Asn Ser Gly Asp Tyr Phe Asp Tyr Trp Gly Gln Gly
            100                 105                 110

Thr Thr Val Thr Val Ser Ser
        115
```

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asn Phe Met Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Thr
                85                  90                  95

Asn Thr Leu Asp Val Leu Phe Gly Gly Gly Thr Lys Leu Thr Val Leu
            100                 105                 110

<210> SEQ ID NO 31
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65              70                  75                  80

Met Glu Leu Ser Gly Leu Arg Ser Glu Asp Thr Ala Val Tyr Tyr Cys
                85                  90                  95

Ala Arg Tyr Glu His Asp Tyr Asp Ser Ser Lys Ala Thr Thr Gly Tyr
            100                 105                 110

Phe Asp Tyr Trp Gly Gln Gly Thr Leu Val Thr Val Ser Ser
        115                 120                 125

<210> SEQ ID NO 32
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Arg
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

```
Pro Asp Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ala Asp Arg Phe Pro Ile Thr Phe Gly Gln Gly Thr Arg Leu Glu Ile
            100                 105                 110

Lys
```

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Asn Trp Ile Arg Gln Ser Pro Ser Arg Gly Leu Glu
             35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Asp Arg Trp Glu Leu Pro Phe Asp Tyr Trp Gly
            100                 105                 110

Gln Gly Thr Thr Val Thr Val Ser Ser
            115                 120
```

<210> SEQ ID NO 34
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Ser Val Val Thr Gln Pro Pro Ser Val Ser Ala Ala Ser Gly Gln
  1               5                  10                  15

Lys Val Ile Ile Ser Cys Ser Gly Ser Asn Ser Asn Ile Val Asn Asn
                 20                  25                  30

Tyr Val Ser Trp Tyr Gln Gln Leu Pro Gly Ala Ala Pro Lys Val Leu
             35                  40                  45

Ile Tyr Ala Asn Asn Lys Arg Pro Ser Gly Ile Pro Asp Arg Phe Ser
 50                  55                  60

Gly Ser Lys Ser Gly Thr Ser Ala Phe Leu Ala Ile Thr Gly Leu Gln
 65                  70                  75                  80

Thr Gly Asp Glu Ala Asp Tyr Tyr Cys Gly Thr Trp Asp Gly Ser Leu
                 85                  90                  95

Asp Val Asp Val Phe Gly Gly Gly Thr Lys Leu Thr Val Leu
            100                 105                 110
```

<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Pro Gly Ile Leu Thr Gly Tyr Tyr Phe Asp Tyr Trp Gly
            100                 105                 110

Gln Gly Thr Leu Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Tyr His
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Thr Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Thr Tyr Pro Leu
                85                  90                  95

Thr Phe Gly Gly Gly Thr Lys Leu Glu Ile Lys
            100                 105

<210> SEQ ID NO 37
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Gln Val Gln Leu Gln Gln Ser Gly Pro Gly Leu Val Lys Pro Ser Gln

```
            1               5                  10                 15
         Thr Leu Ser Leu Thr Cys Ala Ile Ser Gly Asp Ser Val Ser Ser Asn
                    20                 25                 30

Ser Ala Ala Trp Asn Trp Ile Arg Gln Ser Pro Ser Arg Gly Leu Glu
                    35                 40                 45

Trp Leu Gly Arg Thr Tyr Tyr Arg Ser Lys Trp Tyr Asn Asp Tyr Ala
                    50                 55                 60

Val Ser Val Lys Ser Arg Ile Thr Ile Asn Pro Asp Thr Ser Lys Asn
          65                 70                 75                 80

Gln Phe Ser Leu Gln Leu Asn Ser Val Thr Pro Glu Asp Thr Ala Val
                            85                 90                 95

Tyr Tyr Cys Ala Met His Ser Gly Tyr Arg Asn Tyr Gly Met Asp Val
                       100                105                110

Trp Gly Gln Gly Thr Thr Val Thr Val Ser Ser
                       115                120

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ser Val Val Thr Gln Pro Pro Ser Val Ser Gly Ala Pro Gly Gln
          1               5                  10                 15

Arg Val Thr Ile Ser Cys Thr Gly Ser Ser Ser Asn Ile Gly Ala Gly
                    20                 25                 30

Tyr Asp Val His Trp Tyr Gln Gln Leu Pro Gly Thr Ala Pro Lys Leu
                    35                 40                 45

Leu Ile Tyr Gly Asn Ser Asn Arg Pro Ser Gly Val Pro Asp Arg Phe
                    50                 55                 60

Ser Gly Ser Lys Ser Gly Thr Ser Ala Ser Leu Ala Ile Thr Gly Leu
          65                 70                 75                 80

Gln Ala Glu Asp Glu Ala Asp Tyr Tyr Cys Gln Ser Tyr Asp Ser Ser
                            85                 90                 95

Leu Ser Gly Ala Val Val Phe Gly Gly Gly Thr Lys Leu Thr Val Leu
                       100                105                110

<210> SEQ ID NO 39
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ala
          1               5                  10                 15

Thr Val Lys Val Ser Cys Thr Ala Ser Gly Phe Pro Phe Arg Asn Tyr
                    20                 25                 30

Ala Met His Trp Val Arg Gln Ala Pro Gly Gln Arg Leu Glu Trp Leu
                    35                 40                 45

Gly Trp Ile Asp Ala Gly Asn Gly Asn Thr Lys Tyr Ser Gln Thr Phe
                    50                 55                 60

His Gly Arg Val Thr Ile Thr Arg Asp Thr Ser Ala Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Asp Leu Leu Trp Pro Tyr Leu Val Thr Ser Gly Gly Ala Phe
                100                 105                 110

Asp Ile Trp Gly Gln Gly Thr Met Val Thr Val Ser Ser
            115                 120                 125

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Tyr Glu Leu Met Gln Pro Pro Ser Thr Ser Gly Thr Pro Gly Gln
1               5                   10                  15

Arg Val Thr Ile Ser Cys Ser Gly Ser Ser Asn Ile Gly Ser His
            20                  25                  30

Ile Val Asn Gly Tyr Gln Gln Phe Pro Gly Ala Ala Pro Gln Leu Leu
        35                  40                  45

Ile Tyr Asn Asp Asp Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala His Tyr Tyr Cys Ser Ala Trp Asp Ile Leu
                85                  90                  95

Lys Gly Pro Val Phe Gly Gly Gly Thr Lys Val Thr Val Leu
            100                 105                 110

<210> SEQ ID NO 41
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Asn Tyr
            20                  25                  30

Tyr Ile His Trp Leu Arg Gln Ala Pro Gly Gln Gly Leu Glu Trp Met
        35                  40                  45

Gly Ile Ile Asn Pro Ser Gly Gly Ser Thr Thr Tyr Ala Gln Lys Phe
    50                  55                  60

Gln Gly Arg Ile Thr Met Thr Arg Asp Thr Ser Thr Asn Thr Leu Tyr
65                  70                  75                  80

Met Glu Leu Ser Ser Leu Arg Ser Glu Asp Thr Ala Ile Tyr Tyr Cys
                85                  90                  95

Ala Arg Arg Asp Cys Arg Gly Pro Ser Cys Tyr Phe Ala Tyr Trp Gly
                100                 105                 110

Gln Gly Thr Thr Val Thr Val Ser Ser
            115                 120
```

```
<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Val Asp Ile Lys
            100                 105

<210> SEQ ID NO 43
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Arg
1               5                   10                  15

Ser Leu Arg Leu Ser Cys Arg Gly Ser Asn Phe Asn Phe Asp Asp Leu
            20                  25                  30

Ala Ile Ser Trp Val Arg Gln Ala Pro Gly Lys Gly Leu Glu Trp Leu
        35                  40                  45

Gly Phe Val Arg Ser Lys Ala Tyr Gly Glu Thr Thr Asp Tyr Val Ala
    50                  55                  60

Ser Val Lys Gly Arg Phe Thr Ile Ser Arg Asp Asp Ser Lys Phe Ile
65                  70                  75                  80

Ala Trp Leu Gln Met Asp Ser Leu Lys Thr Asp Thr Ala Val Tyr
                85                  90                  95

Tyr Cys Thr Thr Phe Asn Tyr Trp Gly Gln Gly Thr Leu Val Thr Val
            100                 105                 110

Ser Ser

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Pro Val Leu Thr Gln Pro Pro Ser Val Ser Val Ala Pro Gly Lys
1               5                   10                  15
```

```
Thr Ala Arg Ile Ser Cys Gly Gly Asn Asn Ile Ala Ser Glu Ala Val
            20                  25                  30

His Trp Tyr Gln Lys Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Arg Ile Ser Arg Val Asp Ala Gly
65                  70                  75                  80

Asp Glu Ala Asp Tyr Tyr Cys Gln Val Trp Asp Arg Thr Thr Asp Gln
                85                  90                  95

Pro Val Phe Gly Gly Gly Thr Lys Leu Thr Val Leu
            100                 105

<210> SEQ ID NO 45
<211> LENGTH: 4
<212> TYPE: PRT
<213> ORGANISM: Unknown
<220> FEATURE:
<223> OTHER INFORMATION: Description of Unknown:
      Hinge region sequence

<400> SEQUENCE: 45

Cys Pro Ser Cys
1

<210> SEQ ID NO 46
<211> LENGTH: 4
<212> TYPE: PRT
<213> ORGANISM: Unknown
<220> FEATURE:
<223> OTHER INFORMATION: Description of Unknown:
      Hinge region sequence

<400> SEQUENCE: 46

Cys Pro Pro Cys
1
```

ANTIBODY THERAPEUTICS THAT BIND CTLA4

RELATED APPLICATIONS

The present application claims priority to U.S. Provisional Application No. 62/116,353, filed on Feb. 13, 2015, the entire contents of which are incorporated by reference in its entirety herein.

TECHNICAL FIELD

The present disclosure provides compositions and methods relating to or derived from anti-CTLA4 antibodies. More specifically, the present disclosure provides fully human antibodies that bind CTLA4, CTLA4-antibody binding fragments and derivatives of such antibodies, and CTLA4-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease requiring either stimulation of immune responses or suppression. Stimulation was achieved using antibodies that block binding of human CTLA4 to human B7 and diseases amenable to treatment by stimulation and augmentation of prolonging of immune responses include cancers of the prostate, kidney, colon, lung or breast; pathogenic infections; diseases associated with the CNS e.g. amyloidogenic diseases including Alzheimer's disease; and diseases with inflammatory or allergic components. Diseases amenable to treatment include graft versus host disease, host versus graft disease, allergy, autoimmune diseases and other inflammatory diseases.

BACKGROUND

The vertebrate immune system requires multiple signals to achieve optimal immune activation; see, e.g., Janeway, Cold Spring Harbor Symp. *Quant. Biol.* 54:1-14 (1989); Paul William E., ed. Raven Press, N.Y., *Fundamental Immunology*, 4th edition (1998), particularly chapters 12 and 13, pages 411 to 478. Interactions between T lymphocytes (T cells) and antigen presenting cells (APC) are essential to the immune response. Levels of many cohesive molecules found on T cells and APC's increase during an immune response (Springer et al., *A. Rev. Immunol.* 5:223-252 (1987); Shaw and Shimuzu, *Current Opinion in Immunology*, Eds. Kindt and Long, 1:92-97 (1988)); and Hemler, *Immunology Today* 9:109-113 (1988)). Increased levels of these molecules may help explain why activated APC's are more effective at stimulating antigen-specific T cell proliferation than are resting APC's (Kaiuchi et al., *J. Immunol.* 131:109-114 (1983); Kreiger et al., *J. Immunol.* 135:2937-2945 (1985); McKenzie, *J. Immunol.* 141:2907-2911 (1988); and Hawrylowicz and Unanue, *J. Immunol.* 141: 4083-4088 (1988)).

T cell immune response is a complex process that involves cell-cell interactions (Springer et al., *A. Rev. Immunol.* 5:223-252 (1987)), particularly between T and accessory cells such as APC's, and production of soluble immune mediators (cytokines or lymphokines) (Dinarello (1987) *New Engl. Jour. Med.* 317:940-945; Sallusto (1997) *J. Exp. Med.* 179:1109-1118). This response is regulated by several T-cell surface receptors, including the T-cell receptor complex (Weiss (1986) *Ann. Rev. Immunol.* 4:593-619) and other "accessory" surface molecules (Allison (1994) *Curr. Opin. Immunol.* 6:414-419; Springer (1987) supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y. (1987)).

CD28 has a single extracellular variable region (V)-like domain (Aruffo and Seed, supra). A homologous molecule, CTLA4 has been identified by differential screening of a murine cytolytic-T cell cDNA library (Brunet (1987) *Nature* 328:267-270).

CTLA4 is a T cell surface molecule that was originally identified by differential screening of a murine cytolytic T cell cDNA library (Brunet et al., *Nature* 328:267-270 (1987)). CTLA4 is also a member of the immunoglobulin (Ig) superfamily; CTLA4 comprises a single extracellular Ig domain. CTLA4 transcripts have been found in T cell populations having cytotoxic activity, suggesting that CTLA4 might function in the cytolytic response (Brunet et al., supra; Brunet et al., *Immunol. Rev.* 103-21-36 (1988)). Researchers have reported the cloning and mapping of a gene for the human counterpart of CTLA4 (Dariavach et al., *Eur. J. Immunol.* 18:1901-1905 (1988)) to the same chromosomal region (2q33-34) as CD28 (Lafage-Pochitaloff et al., *Immunogenetics* 31:198-201 (1990)). Sequence comparison between this human CTLA4 DNA and that encoding CD28 proteins reveals significant homology of sequence, with the greatest degree of homology in the juxtamembrane and cytoplasmic regions (Brunet et al., 1988, supra; Dariavach et al., 1988, supra).

Some studies have suggested that CTLA4 has an analogous function as a secondary costimulator (Linsley et al., *J. Exp. Med.* 176:1595-1604 (1992); Wu et al., *J. Exp. Med.* 185:1327-1335 (1997) and U.S. Pat. Nos. 5,977,318; 5,968, 510; 5,885,796; and 5,885,579). However, others have reported that CTLA4 has an opposing role as a dampener of T cell activation (Krummel (1995) *J. Exp. Med.* 182:459-465); Krummel et al., *Int'l Immunol.* 8:519-523 (1996); Chambers et al., *Immunity.* 7:885-895 (1997)). It has been reported that CTLA4 deficient mice suffer from massive lymphoproliferation (Chambers et al., supra). It has been reported that CTLA4 blockade augments T cell responses in vitro (Walunas et al., *Immunity.* 1:405-413 (1994)) and in vivo (Kearney (1995) *J. Immunol.* 155:1032-1036), exacerbates antitumor immunity (Leach (1996) *Science.* 271:1734-1736), and enhances an induced autoimmune disease (Luhder (1998) *J Exp. Med.* 187:427-432). It has also been reported that CTLA4 has an alternative or additional impact on the initial character of the T cell immune response (Chambers (1997) *Curr. Opin. Immunol.* 9:396-404; Bluestone (1997) *J. Immunol.* 158:1989-1993; *Thompson* (1997) *Immunity* 7:445-450). This is consistent with the observation that some autoimmune patients have autoantibodies to CTLA4. It is possible that CTLA4 blocking antibodies have a pathogenic role in these patients (Matsui (1999) *J. Immunol.* 162:4328-4335).

Non-human CTLA4 antibodies have been used in the various studies. However, one of the major impediments facing the development of in vivo therapeutic and diagnostic applications for antibodies in humans is the intrinsic immunogenicity of non-human immunoglobulins. For example, when immunocompetent human patients are administered therapeutic doses of rodent monoclonal antibodies, the patients produce antibodies against the rodent immunoglobulin sequences; these human anti-mouse antibodies (HAMA) neutralize the therapeutic antibodies and can cause acute toxicity. These and other deficiencies in the previous antibodies are overcome by the provision of fully human antibodies to CTLA4 by the present disclosure.

SUMMARY

This invention pertains to binding proteins capable of binding to CTLA4, including anti-CTLA4 antibodies, and antigen-binding fragments thereof.

In one aspect, the present disclosure provides an isolated fully human anti-CTLA4 antibody of an IgG class that binds to a CTLA4 epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, and SEQ ID NO: 43, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, and SEQ ID NO: 44. In one embodiment, the fully human antibody has both a heavy chain and a light chain wherein the antibody has a heavy chain/light chain variable domain sequence selected from the group consisting of SEQ ID NO. 1/SEQ ID NO. 2 (called A1 herein), SEQ ID NO. 3/SEQ ID NO. 4 (called A2 herein), SEQ ID NO. 5/SEQ ID NO. 6 (called A4 herein), SEQ ID NO. 7/SEQ ID NO. 8 (called A7 herein), SEQ ID NO. 9/SEQ ID NO. 10 (called A12 herein), SEQ ID NO. 11/SEQ ID NO. 12 (called B6 herein), SEQ ID NO. 13/SEQ ID NO. 14 (called C2 herein), SEQ ID NO. 15/SEQ ID NO. 16 (called D6 herein), SEQ ID NO. 17/SEQ ID NO. 18 (called F1 herein), SEQ ID NO. 19/SEQ ID NO. 20 (called F3 herein), SEQ ID NO. 21/SEQ ID NO. 22 (called F5 herein), SEQ ID NO. 23/SEQ ID NO. 24 (called F6 herein), SEQ ID NO. 25/SEQ ID NO. 26 (called F7 herein), SEQ ID NO. 27/SEQ ID NO. 28 (called G1 herein), SEQ ID NO. 29/SEQ ID NO. 30 (called G2 herein), SEQ ID NO. 31/SEQ ID NO. 32 (called G3 herein), SEQ ID NO. 33/SEQ ID NO. 34 (called G5 herein), SEQ ID NO. 35/SEQ ID NO. 36 (called G12 herein), SEQ ID NO. 37/SEQ ID NO. 38 (called D5 herein), SEQ ID NO. 39/SEQ ID NO. 40 (called E7 herein), SEQ ID NO. 41/SEQ ID NO. 42 (called E8 herein), and SEQ ID NO: 43/SEQ ID NO: 44 (called CT1E1 herein).

In another aspect, the present disclosure provides an anti-CTLA4 Fab fully human antibody fragment comprising a heavy chain variable domain comprising a sequence that is at least 95% identical to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, and SEQ ID NO: 43, and comprising a light chain variable domain comprising a sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, and SEQ ID NO: 44. In one embodiment, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, and SEQ ID NO: 43/SEQ ID NO. 44.

The present disclosure further provides a single chain human antibody having a heavy chain variable domain and a light chain variable domain connected by a peptide linker, wherein the heavy chain variable domain comprises an amino acid sequence that is at least 95% identical to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, and SEQ ID NO: 43, and wherein the light chain variable domain comprises an amino acid sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, and SEQ ID NO: 44. In certain embodiments, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, and SEQ ID NO. 43/SEQ ID NO. 44.

Also included in the invention, is an isolated anti-CTLA4 antibody, or antigen-binding fragment thereof, comprising a heavy chain variable domain comprising complementarity determining regions (CDRs) as set forth in a heavy chain variable region amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and SEQ ID NO: 43; and comprising a light chain variable region comprising CDRs as set forth in a light chain variable region amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and SEQ ID NO: 44.

The present disclosure further provides a method for treating a disease requiring either stimulation of immune responses or suppression, comprising administering an anti-CTLA4 polypeptide, wherein the anti-CTLA4 polypeptide is selected from the group consisting of an isolated fully human antibody of an IgG class that binds to CTLA4 and comprises a heavy chain variable domain and a light chain variable domain; an anti-CTLA4 fully human antibody Fab fragment comprising a heavy chain variable domain and a light chain variable domain; and a single chain human antibody comprising a heavy chain variable domain and a light chain variable domain, wherein the heavy chain variable domain and the light chain variable domain are connected via a peptide linker; wherein the heavy chain variable domain comprises an amino acid sequence that is at least 95% identical to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, and SEQ ID NO. 43, and wherein the light chain variable domain comprises an amino acid sequence that is at least 95% identical to an amino acid selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, and SEQ ID NO. 44.

In certain embodiments, the fully human antibody or antibody fragment has both a heavy chain and a light chain wherein the antibody or antibody fragment comprises a heavy chain/light chain variable domain sequence selected from the group consisting of SEQ ID NO. 1/SEQ ID NO. 2 (called A1 herein), SEQ ID NO. 3/SEQ ID NO. 4 (called A2 herein), SEQ ID NO. 5/SEQ ID NO. 6 (called A4 herein), SEQ ID NO. 7/SEQ ID NO. 8 (called A7 herein), SEQ ID NO. 9/SEQ ID NO. 10 (called A12 herein), SEQ ID NO. 11/SEQ ID NO. 12 (called B6 herein), SEQ ID NO. 13/SEQ ID NO. 14 (called C2 herein), SEQ ID NO. 15/SEQ ID NO. 16 (called D6 herein), SEQ ID NO. 17/SEQ ID NO. 18 (called F1 herein), SEQ ID NO. 19/SEQ ID NO. 20 (called F3 herein), SEQ ID NO. 21/SEQ ID NO. 22 (called F5 herein), SEQ ID NO. 23/SEQ ID NO. 24 (called F6 herein), SEQ ID NO. 25/SEQ ID NO. 26 (called F7 herein), SEQ ID NO. 27/SEQ ID NO. 28 (called G1 herein), SEQ ID NO. 29/SEQ ID NO. 30 (called G2 herein), SEQ ID NO. 31/SEQ ID NO. 32 (called G3 herein), SEQ ID NO. 33/SEQ ID NO. 34 (called G5 herein), SEQ ID NO. 35/SEQ ID NO. 36 (called G12 herein), SEQ ID NO. 37/SEQ ID NO. 38 (called D5 herein), SEQ ID NO. 39/SEQ ID NO. 40 (called E7 herein), SEQ ID NO. 41/SEQ ID NO. 42 (called E8 herein), and SEQ ID NO. 43/SEQ ID NO. 44 (called CT1E1 herein).

In certain embodiments, the antibody, or antigen-binding fragment thereof, of the invention has a $K_D$ of at least $1 \times 10^{-6}$M. In other embodiments, the antibody, or antigen-binding fragment thereof, of the invention has a $K_D$ of at least $1 \times 10^{-7}$M. In other embodiments, the antibody, or antigen-binding fragment thereof, of the invention has a $K_D$ of at least $1 \times 10^{-8}$M.

In certain embodiments, the antibody is an IgG1 isotype. In other embodiments, the antibody is an IgG4 isotype.

In certain embodiments, the antibody, or antigen-binding fragment, described herein is recombinant.

The invention also provides pharmaceutical compositions comprising an effective amount of an anti-CTLA4 antibodies or fragments disclosed herein, and a pharmaceutically acceptable carrier.

In certain embodiments, the invention features a method of treating cancer in a human subject in need thereof, comprising administering an effective amount of an anti-CTLA4 antibody, or antigen-binding fragment thereof, disclosed herein to the subject, such that cancer is treated.

In a preferred embodiment, the cancer is associated with detrimental CTLA4 activity. Examples of such types of cancer include, but are not limited to, bladder cancer, blood cancer, brain cancer, breast cancer, colon cancer, fibrosarcoma, lung cancer, ovarian cancer, prostate cancer, melanoma, lymphoma, mesothelioma, and plasmacytoma.

In other embodiments, the disease is selected from the group consisting of cancers of the prostate, kidney, colon, lung or breast; pathogenic infections; diseases associated with the CNS, amyloidogenic Alzheimer's disease; and diseases with inflammatory or allergic components, graft versus host disease, host versus graft disease, allergy, autoimmune diseases and other inflammatory diseases.

DETAILED DESCRIPTION

Definitions

Figure 1:
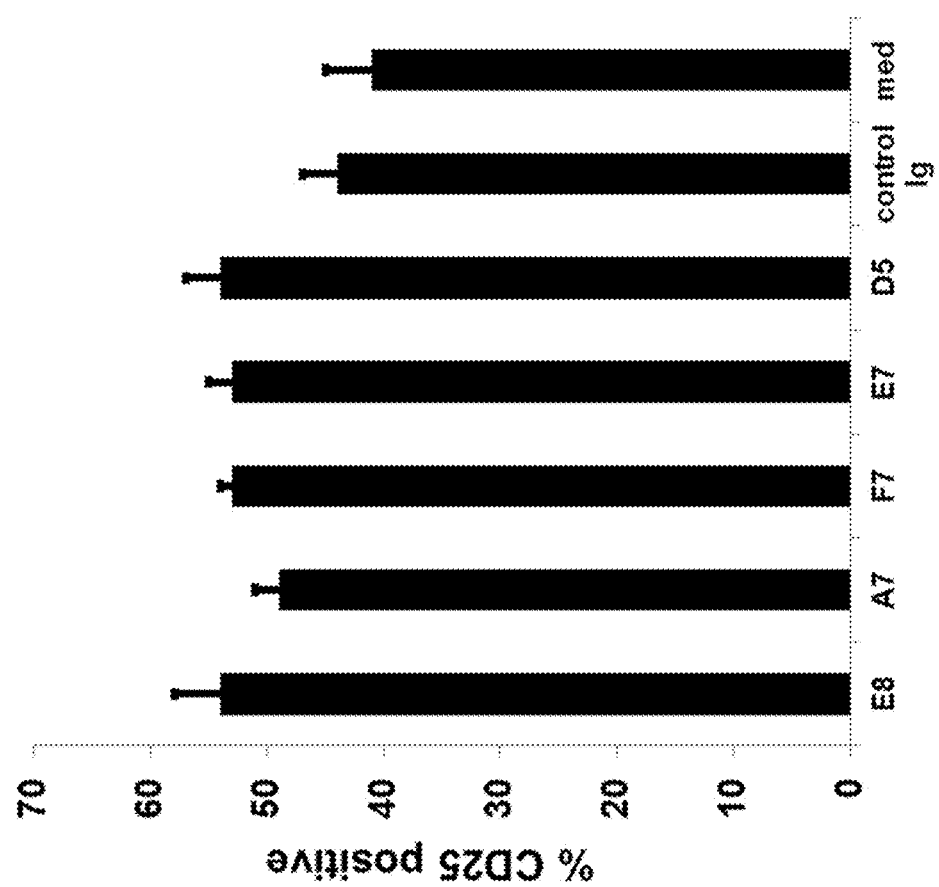
FIG. 1 shows functional activity of the listed anti-CTLA4 antibodies by their ability to augment T cell activation. The level of CD25 expression was higher in the cultures where anti-CTLA4 antibodies had been added. The control antibody used (control Ig) is an isotype matched, non-specific (i.e., does not bind CTLA4) antibody.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, a variant of an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of an immunoglobulin. An "immunoglobulin" is a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, in one embodiment, the anti-CTLA4 antibodies disclosed herein are characterized by their variable domain region sequences in the heavy (VH) and light (VL) amino acid sequences. In one embodiment, the preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Other numbering systems for the amino acids in immunoglobulin chains include IMGT™ (international ImMunoGeneTics information system; Lefranc et al, Dev. Comp. Immunol. 29:185-203; 2005) and AHo (Honegger and Pluckthun, J. Mol. Biol. 309(3):657-670; 2001).

An "antibody" refers to an intact immunoglobulin, or to an antigen binding portion thereof that competes with the intact antibody for specific binding, unless otherwise specified.

In one embodiment, an antibody comprises a heavy chain variable domain, a light chain variable domain, a light chain constant region ($C_L$), and heavy chain constant regions $C_{H1}$, $C_{H2}$ and $C_{H3}$. The heavy and light chain variable domain sequences may be selected from those described herein in SEQ ID Nos: 1 to 44.

Antigen binding portions of an antibody may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

In certain embodiments, antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific."

The term "monospecific", as used herein, refers to an antibody that displays an affinity for one particular epitope. Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody fragment" or "antigen binding fragment of an antibody" comprises a portion of an intact antibody, and preferably comprises the antibody antigen binding or variable domains. Examples of an antibody fragment include a Fab, an Fab', an F(ab')$_2$, an Fv fragment, and a linear antibody.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App. Pub 2002/02512; 2004/0202995; 2004/0038291; 2004/0009507; 2003/0039958, and Ward et al., *Nature* 341:544-546, 1989).

A single-chain antibody (scFv) is an antibody fragment in which a $V_L$ and a $V_H$ region are joined via a linker (e.g., a synthetic sequence of amino acid residues) to form a continuous protein chain, wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83).

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An antigen binding protein, such as an antibody, may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains of the antibody are derived from human immunoglobulin sequences (referred to as a "fully human antibody"). These antibodies may be prepared in a variety of ways, examples of which are described below, including through the immunization with an antigen of interest of a mouse that is genetically modified to express antibodies derived from human heavy and/or light chain-encoding genes. In a preferred embodiment, a fully human antibody is made using recombinant methods such that the glycosylation pattern of the antibody is different than an antibody having the same sequence if it were to exist in nature.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CTLA4 antibody. In another embodiment, all of the CDRs are derived from a human anti-CTLA4 antibody. In another embodiment, the CDRs from more than one human anti-CTLA4 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-CTLA4 antibody, and the CDRs from the heavy chain from a third anti-CTLA4 antibody. Other combinations are possible.

Further, the framework regions may be derived from one of the same anti-CTLA4 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind CTLA4).

A "neutralizing antibody" or an "inhibitory antibody" is an antagonist antibody that inhibits CTLA4 activity, e.g., inhibits the proteolytic activation of CTLA4. In one embodiment, proteolytic activation of CTLA4 is determined when an excess of the anti-CTLA4 antibody reduces the amount of activation by at least about 20% using an assay such as those described herein in the Examples. In various embodiments, the antigen binding protein reduces the amount of amount of proteolytic activation of CTLA4 by at least 30%, 40%, 50%, 60%, 70%, 75%, 80%, 85%, 90%, 95%, 97%, 99%, and 99.9%.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CTLA4) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with an expression vector (or possibly more than one expression vector, typically two expression vectors) comprising the coding sequence of the antibody, where said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof that binds CTLA4, which is sufficient to effect treatment, prognosis or diagnosis of a disease associated with CTLA4 dependent signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material and/or chemicals. In one embodiment, an isolated antibody is substantially free of other proteins from the same species. In one embodiment, an isolated antibody is expressed by a cell from a different species and is substantially free of other proteins from the difference species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

CTLA4 Antigen Binding Proteins

The present invention pertains to CTLA4 binding proteins, particularly anti-CTLA4 antibodies, or antigen-binding portions thereof, that bind CTLA4, and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human CTLA4, to inhibit CTLA4 activity, either in vitro or in vivo, and to prevent or treat disorders such as cancer are also encompassed by the invention.

As described in Table 4 below, included in the invention are novel antibody heavy and light chain variable regions that are specific to CTLA4. In one embodiment, the invention provides an anti-CTLA4 antibody, or an antigen-binding fragment thereof, that comprises a heavy chain having a variable domain comprising an amino acid sequence as set forth in any one of SEQ ID Nos: 1, 3, 5, 7, 9, 11, 13, 15, 17, 19, 21, 23, 25, 27, 29, 31, 33, 35, 37, 39, 41, and 43. In one embodiment, the invention provides an anti-CTLA4 antibody, or an antigen-binding fragment thereof, that comprises a light chain having a variable domain comprising an amino acid sequence as set forth in any one of SEQ ID Nos: 2, 4, 6, 8, 10, 12, 14, 16, 18, 20, 22, 24, 26, 28, 30, 32, 34, 36, 38, 40, 42, and 44. In one embodiment, the invention provides an anti-CTLA4 antibody, or an antigen-binding fragment thereof, that comprises a heavy chain having a variable domain comprising an amino acid sequence as set forth in any one of SEQ ID Nos: 1, 3, 5, 7, 9, 11, 13, 15, 17, 19, 21, 23, 25, 27, 29, 31, 33, 35, 37, 39, 41, and 43; and comprises a light chain having a variable domain comprising an amino acid sequence as set forth in any one of SEQ ID Nos: 2, 4, 6, 8, 10, 12, 14, 16, 18, 20, 22, 24, 26, 28, 30, 32, 34, 36, 38, 40, 42, and 44.

Complementarity determining regions (CDRs) are known as hypervariable regions both in the light chain and the heavy chain variable domains. The more highly conserved portions of variable domains are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself. Alternative numbering is set forth in Chothia et al., J. Mol. Biol. 196:901-917 (1987) and MacCallum et al., J. Mol. Biol. 262:732-745 (1996), although as in Kabat, the FR boundaries are separated by the respective CDR termini as described above. See also Chothia et al., Nature 342, pp. 877-883 (1989) and S. Dubel, ed., Handbook of Therapeutic Antibodies, 3rd ed., WILEY-VCH Verlag GmbH and Co. (2007), where the definitions include overlapping or subsets of amino acid residues when compared against each other.

In certain embodiments, the present invention provides an anti-CTLA4 antibody comprising the CDRs of the heavy and light chain variable domains described in Table 4 (SEQ ID Nos: 1-44). For example, the invention provides an anti-CTLA4 antibody, or antigen-binding fragment thereof, comprising a heavy chain variable region having the CDRs described in an amino acid sequence as set forth in any one of SEQ ID Nos: 1, 3, 5, 7, 9, 11, 13, 15, 17, 19, 21, 23, 25, 27, 29, 31, 33, 35, 37, 39, 41, and 43. In one embodiment, the invention provides an anti-CTLA4 antibody, or antigen-binding fragment thereof, comprising a light chain variable region having the CDRs described in an amino acid sequence as set forth in any one of SEQ ID Nos: 2, 4, 6, 8, 10, 12, 14, 16, 18, 20, 22, 24, 26, 28, 30, 32, 34, 36, 38, 40, 42, and 44. In one embodiment, the invention provides an anti-CTLA4 antibody, or antigen-binding fragment thereof, comprising a light chain variable region having the CDRs described in an amino acid sequence as set forth in any one of SEQ ID Nos: 2, 4, 6, 8, 10, 12, 14, 16, 18, 20, 22, 24, 26, 28, 30, 32, 34, 36, 38, 40, 42, and 44; and comprising a heavy chain variable region having the CDRs described in an amino acid sequence as set forth in any one of SEQ ID Nos: 1, 3, 5, 7, 9, 11, 13, 15, 17, 19, 21, 23, 25, 27, 29, 31, 33, 35, 37, 39, 41, and 43.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In one embodiment, the present disclosure provides an isolated fully human antibody of an IgG class that binds to a CTLA4 epitope, that has a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44.

In one embodiment, the isolated fully human antibody has both a heavy chain and a light chain wherein the antibody has a heavy chain/light chain variable domain sequence selected from the group consisting of SEQ ID NO. 1/SEQ ID NO. 2 (called A1 herein), SEQ ID NO. 3/SEQ ID NO. 4 (called A2 herein), SEQ ID NO. 5/SEQ ID NO. 6 (called A4 herein), SEQ ID NO. 7/SEQ ID NO. 8 (called A7 herein), SEQ ID NO. 9/SEQ ID NO. 10 (called A12 herein), SEQ ID NO. 11/SEQ ID NO. 12 (called B6 herein), SEQ ID NO. 13/SEQ ID NO. 14 (called C2 herein), SEQ ID NO. 15/SEQ ID NO. 16 (called D6 herein), SEQ ID NO. 17/SEQ ID NO. 18 (called F1 herein), SEQ ID NO. 19/SEQ ID NO. 20 (called F3 herein), SEQ ID NO. 21/SEQ ID NO. 22 (called F5 herein), SEQ ID NO. 23/SEQ ID NO. 24 (called F6 herein), SEQ ID NO. 25/SEQ ID NO. 26 (called F7 herein), SEQ ID NO. 27/SEQ ID NO. 28 (called G1 herein), SEQ ID NO. 29/SEQ ID NO. 30 (called G2 herein), SEQ ID NO. 31/SEQ ID NO. 32 (called G3 herein), SEQ ID NO. 33/SEQ ID NO. 34 (called G5 herein), SEQ ID NO. 35/SEQ ID NO. 36 (called G12 herein), SEQ ID NO. 37/SEQ ID NO. 38 (called D5 herein), SEQ ID NO. 39/SEQ ID NO. 40 (called E7 herein), SEQ ID NO. 41/SEQ ID NO. 42 (called E8 herein), SEQ ID NO. 43/SEQ ID NO. 44 (called CT1E1 herein), and combinations thereof.

In one embodiment, the invention provides an anti-CTLA4 antibody, or an antigen-binding fragment thereof, comprising a heavy chain comprising a CDR3 domain as set forth in any one of SEQ ID Nos: 1, 3, 5, 7, 9, 11, 13, 15, 17, 19, 21, 23, 25, 27, 29, 31, 33, 35, 37, 39, 41, and 43 and comprising a variable domain comprising an amino acid sequence that has at least 95%, at least 96%, at least 97%, at least 98%, or at least 99% identical to a sequence as set forth in any one of SEQ ID Nos: 1, 3, 5, 7, 9, 11, 13, 15, 17, 19, 21, 23, 25, 27, 29, 31, 33, 35, 37, 39, 41, and 43. In one embodiment, the invention provides an anti-CTLA4 antibody, or an antigen-binding fragment thereof, comprising a light chain comprising a CDR3 domain as set forth in any one of SEQ ID Nos: 2, 4, 6, 8, 10, 12, 14, 16, 18, 20, 22, 24, 26, 28, 30, 32, 34, 36, 38, 40, 42, and 44 and having a light chain variable domain comprising an amino acid sequence that has at least 95%, at least 96%, at least 97%, at least 98%, or at least 99% identical to a sequence as set forth in any one of SEQ ID Nos: 2, 4, 6, 8, 10, 12, 14, 16, 18, 20, 22, 24, 26, 28, 30, 32, 34, 36, 38, 40, 42, and 44. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to CTLA4 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or antigen-binding fragment thereof, having the antigen binding regions of antibody A1. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 2. In one embodiment, the invention is directed to an antibody having a heavy chain variable domain comprising the CDRs of SEQ ID NO: 1, and a light chain variable domain comprising the CDRs of SEQ ID NO: 2. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 1, and comprises a light chain variable region having an amino acid sequence that is at least 95% identical, at least 96% identical, at least 97% identical, at least 98% identical, or at least 99% identical to the sequence set forth in SEQ ID NO. 2. The antibody may further be an IgG1 or an IgG4 isotype.

In one embodiment, the present invention is directed to an antibody, or antigen-binding fragment thereof, having the antigen binding regions of antibody A2. In one embodiment, the invention provides an antibody, or antigen-binding fragment thereof, comprising a heavy chain variable domain sequence as set forth in SEQ ID NO: 3, and a light chain variable domain sequence as set forth in SEQ ID NO: 4. In one embodiment, the invention is directed to an antibody having a heavy chain variable domain comprising the CDRs of SEQ ID NO: 3, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 3, and comprises a light chain variable region having an amino acid sequence that is at least 95% identical, at least 96% identical, at least 97% identical, at least 98% identical, or at least 99% identical to the sequence set forth in SEQ ID NO. 4. The antibody may further be an IgG1 or an IgG4 isotype.

In one embodiment, the present invention is directed to an antibody, or antigen-binding fragment thereof, having the antigen binding regions of antibody A4. In one embodiment, the invention provides an antibody, or antigen-binding fragment thereof, comprising a heavy chain variable domain sequence as set forth in SEQ ID NO: 5, and a light chain variable domain sequence as set forth in SEQ ID NO: 6. In one embodiment, the invention is directed to an antibody having a heavy chain variable domain comprising the CDRs of SEQ ID NO: 5, and a light chain variable domain comprising the CDRs of SEQ ID NO: 6. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 5, and comprises a light chain variable region having an amino acid sequence that is at least 95% identical, at least 96% identical, at least 97% identical, at least 98% identical, or at least 99% identical to the sequence set forth in SEQ ID NO. 6. The antibody may further be an IgG1 or an IgG4 isotype.

In one embodiment, the present invention is directed to an antibody, or antigen-binding fragment thereof, having the antigen binding regions of antibody A7. In one embodiment, the invention provides an antibody, or antigen-binding fragment thereof, comprising a heavy chain variable domain sequence as set forth in SEQ ID NO: 7, and a light chain variable domain sequence as set forth in SEQ ID NO: 8. In one embodiment, the invention is directed to an antibody having a heavy chain variable domain comprising the CDRs of SEQ ID NO: 7, and a light chain variable domain comprising the CDRs of SEQ ID NO: 8. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 7, and comprises a light chain variable region having an amino acid sequence that is at least 95% identical, at least 96% identical, at least 97% identical, at least 98% identical, or at least 99% identical to the sequence set forth in SEQ ID NO. 8. The antibody may further be an IgG1 or an IgG4 isotype.

In one embodiment, the present invention is directed to an antibody, or antigen-binding fragment thereof, having the antigen binding regions of antibody A12. In one embodiment, the invention provides an antibody, or antigen-binding fragment thereof, comprising a heavy chain variable domain sequence as set forth in SEQ ID NO: 9, and a light chain variable domain sequence as set forth in SEQ ID NO: 10. In one embodiment, the invention is directed to an antibody having a heavy chain variable domain comprising the CDRs of SEQ ID NO: 9, and a light chain variable domain comprising the CDRs of SEQ ID NO: 10. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 9, and comprises a light chain variable region having an amino acid sequence that is at least 95% identical, at least 96% identical, at least 97% identical, at least 98% identical, or at least 99% identical to the sequence set forth in SEQ ID NO. 10. The antibody may further be an IgG1 or an IgG4 isotype.

In one embodiment, the present invention is directed to an antibody, or antigen-binding fragment thereof, having the antigen binding regions of antibody B6. In one embodiment, the invention provides an antibody, or antigen-binding fragment thereof, comprising a heavy chain variable domain sequence as set forth in SEQ ID NO: 11, and a light chain variable domain sequence as set forth in SEQ ID NO: 12. In one embodiment, the invention is directed to an antibody having a heavy chain variable domain comprising the CDRs of SEQ ID NO: 11, and a light chain variable domain comprising the CDRs of SEQ ID NO: 12. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 11, and comprises a light chain variable region having an amino acid sequence that is at least 95% identical, at least 96% identical, at least 97% identical, at least 98% identical, or at least 99% identical to the sequence set forth in SEQ ID NO. 12. The antibody may further be an IgG1 or an IgG4 isotype.

In one embodiment, the present invention is directed to an antibody, or antigen-binding fragment thereof, having the antigen binding regions of antibody C2. In one embodiment, the invention provides an antibody, or antigen-binding fragment thereof, comprising a heavy chain variable domain sequence as set forth in SEQ ID NO: 13, and a light chain variable domain sequence as set forth in SEQ ID NO: 14. In one embodiment, the invention is directed to an antibody having a heavy chain variable domain comprising the CDRs of SEQ ID NO: 13, and a light chain variable domain comprising the CDRs of SEQ ID NO: 14. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 13, and comprises a light chain variable region having an amino acid sequence that is at least 95% identical, at least 96% identical, at least 97% identical, at least 98% identical, or at least 99% identical to the sequence set forth in SEQ ID NO. 14. The antibody may further be an IgG1 or an IgG4 isotype.

In one embodiment, the present invention is directed to an antibody, or antigen-binding fragment thereof, having the antigen binding regions of antibody D6. In one embodiment, the invention provides an antibody, or antigen-binding fragment thereof, comprising a heavy chain variable domain sequence as set forth in SEQ ID NO: 15, and a light chain variable domain sequence as set forth in SEQ ID NO: 16. In one embodiment, the invention is directed to an antibody having a heavy chain variable domain comprising the CDRs of SEQ ID NO: 15, and a light chain variable domain comprising the CDRs of SEQ ID NO: 16. It should be noted that the D6 and the A1 antibodies comprise the same heavy and light chain variable sequences. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 15, and comprises a light chain variable region having an amino acid sequence that is at least 95% identical, at least 96% identical, at least 97% identical, at least 98% identical, or at least 99% identical to the sequence set forth in SEQ ID NO. 16. The antibody may further be an IgG1 or an IgG4 isotype.

In one embodiment, the present invention is directed to an antibody, or antigen-binding fragment thereof, having the antigen binding regions of antibody F1. In one embodiment, the invention provides an antibody, or antigen-binding fragment thereof, comprising a heavy chain variable domain sequence as set forth in SEQ ID NO: 17, and a light chain variable domain sequence as set forth in SEQ ID NO: 18. In one embodiment, the invention is directed to an antibody having a heavy chain variable domain comprising the CDRs of SEQ ID NO: 17, and a light chain variable domain comprising the CDRs of SEQ ID NO: 18. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 17, and comprises a light chain variable region having an amino acid sequence that is at least 95% identical, at least 96% identical, at least 97% identical, at least 98% identical, or at least 99% identical to the sequence set forth in SEQ ID NO. 18. The antibody may further be an IgG1 or an IgG4 isotype.

In one embodiment, the present invention is directed to an antibody, or antigen-binding fragment thereof, having the antigen binding regions of antibody F3. In one embodiment, the invention provides an antibody, or antigen-binding fragment thereof, comprising a heavy chain variable domain sequence as set forth in SEQ ID NO: 19, and a light chain variable domain sequence as set forth in SEQ ID NO: 20. In one embodiment, the invention is directed to an antibody having a heavy chain variable domain comprising the CDRs of SEQ ID NO: 19, and a light chain variable domain comprising the CDRs of SEQ ID NO: 20. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 19, and comprises a light chain variable region having an amino acid sequence that is at least 95% identical, at least 96% identical, at least 97% identical, at least 98% identical, or at least 99% identical to the sequence set forth in SEQ ID NO. 20. The antibody may further be an IgG1 or an IgG4 isotype.

In one embodiment, the present invention is directed to an antibody, or antigen-binding fragment thereof, having the antigen binding regions of antibody F5. In one embodiment, the invention provides an antibody, or antigen-binding fragment thereof, comprising a heavy chain variable domain sequence as set forth in SEQ ID NO: 21, and a light chain variable domain sequence as set forth in SEQ ID NO: 22. In one embodiment, the invention is directed to an antibody having a heavy chain variable domain comprising the CDRs of SEQ ID NO: 21, and a light chain variable domain comprising the CDRs of SEQ ID NO: 22. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 21, and comprises a light chain variable region having an amino acid sequence that is at least 95% identical, at least 96% identical, at least 97% identical, at least 98% identical, or at least 99% identical to the sequence set forth in SEQ ID NO. 22. The antibody may further be an IgG1 or an IgG4 isotype.

In one embodiment, the present invention is directed to an antibody, or antigen-binding fragment thereof, having the antigen binding regions of antibody F6. In one embodiment, the invention provides an antibody, or antigen-binding fragment thereof, comprising a heavy chain variable domain sequence as set forth in SEQ ID NO: 23, and a light chain variable domain sequence as set forth in SEQ ID NO: 24. In one embodiment, the invention is directed to an antibody having a heavy chain variable domain comprising the CDRs of SEQ ID NO: 23, and a light chain variable domain comprising the CDRs of SEQ ID NO: 24. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 23, and comprises a light chain variable region having an amino acid sequence that is at least 95% identical, at least 96% identical, at least 97% identical, at least 98% identical, or at least 99% identical to the sequence set forth in SEQ ID NO. 24. The antibody may further be an IgG1 or an IgG4 isotype.

In one embodiment, the present invention is directed to an antibody, or antigen-binding fragment thereof, having the antigen binding regions of antibody F7. In one embodiment, the invention provides an antibody, or antigen-binding fragment thereof, comprising a heavy chain variable domain sequence as set forth in SEQ ID NO: 25, and a light chain variable domain sequence as set forth in SEQ ID NO: 26. In one embodiment, the invention is directed to an antibody having a heavy chain variable domain comprising the CDRs of SEQ ID NO: 25, and a light chain variable domain comprising the CDRs of SEQ ID NO: 26. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 25, and comprises a light chain variable region having an amino acid sequence that is at least 95% identical, at least 96% identical, at least 97% identical, at least 98% identical, or at least 99% identical to the sequence set forth in SEQ ID NO. 26. The antibody may further be an IgG1 or an IgG4 isotype.

In one embodiment, the present invention is directed to an antibody, or antigen-binding fragment thereof, having the antigen binding regions of antibody G1. In one embodiment, the invention provides an antibody, or antigen-binding fragment thereof, comprising a heavy chain variable domain sequence as set forth in SEQ ID NO: 27, and a light chain variable domain sequence as set forth in SEQ ID NO: 28. In one embodiment, the invention is directed to an antibody having a heavy chain variable domain comprising the CDRs of SEQ ID NO: 27, and a light chain variable domain comprising the CDRs of SEQ ID NO: 28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 27, and comprises a light chain variable region having an amino acid sequence that is at least 95% identical, at least 96% identical, at least 97% identical, at least 98% identical, or at least 99% identical to the sequence set forth in SEQ ID NO. 28. The antibody may further be an IgG1 or an IgG4 isotype.

In one embodiment, the present invention is directed to an antibody, or antigen-binding fragment thereof, having the antigen binding regions of antibody G2. In one embodiment, the invention provides an antibody, or antigen-binding fragment thereof, comprising a heavy chain variable domain sequence as set forth in SEQ ID NO: 29, and a light chain variable domain sequence as set forth in SEQ ID NO: 30. In one embodiment, the invention is directed to an antibody having a heavy chain variable domain comprising the CDRs of SEQ ID NO: 29, and a light chain variable domain comprising the CDRs of SEQ ID NO: 30. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 29, and comprises a light chain variable region having an amino acid sequence that is at least 95% identical, at least 96% identical, at least 97% identical, at least 98% identical, or at least 99% identical to the sequence set forth in SEQ ID NO. 30. The antibody may further be an IgG1 or an IgG4 isotype.

In one embodiment, the present invention is directed to an antibody, or antigen-binding fragment thereof, having the antigen binding regions of antibody G3. In one embodiment, the invention provides an antibody, or antigen-binding fragment thereof, comprising a heavy chain variable domain sequence as set forth in SEQ ID NO: 31, and a light chain variable domain sequence as set forth in SEQ ID NO: 32. In one embodiment, the invention is directed to an antibody having a heavy chain variable domain comprising the CDRs of SEQ ID NO: 31, and a light chain variable domain comprising the CDRs of SEQ ID NO: 32. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 31, and comprises a light chain variable region having an amino acid sequence that is at least 95% identical, at least 96% identical, at least 97% identical, at least 98% identical, or at least 99% identical to the sequence set forth in SEQ ID NO. 32. The antibody may further be an IgG1 or an IgG4 isotype.

In one embodiment, the present invention is directed to an antibody, or antigen-binding fragment thereof, having the antigen binding regions of antibody G5. In one embodiment, the invention provides an antibody, or antigen-binding fragment thereof, comprising a heavy chain variable domain sequence as set forth in SEQ ID NO: 33, and a light chain variable domain sequence as set forth in SEQ ID NO: 34. In one embodiment, the invention is directed to an antibody having a heavy chain variable domain comprising the CDRs of SEQ ID NO: 33, and a light chain variable domain comprising the CDRs of SEQ ID NO: 34. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 33, and comprises a light chain variable region having an amino acid sequence that is at least 95% identical, at least 96% identical, at least 97% identical, at least 98% identical, or at least 99% identical to the sequence set forth in SEQ ID NO. 34. The antibody may further be an IgG1 or an IgG4 isotype.

In one embodiment, the present invention is directed to an antibody, or antigen-binding fragment thereof, having the antigen binding regions of antibody G12. In one embodiment, the invention provides an antibody, or antigen-binding fragment thereof, comprising a heavy chain variable domain sequence as set forth in SEQ ID NO: 35, and a light chain variable domain sequence as set forth in SEQ ID NO: 36. In one embodiment, the invention is directed to an antibody having a heavy chain variable domain comprising the CDRs of SEQ ID NO: 35, and a light chain variable domain comprising the CDRs of SEQ ID NO: 36. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 35, and comprises a light chain variable region having an amino acid sequence that is at least 95% identical, at least 96% identical, at least 97% identical, at least 98% identical, or at least 99% identical to the sequence set forth in SEQ ID NO. 36. The antibody may further be an IgG1 or an IgG4 isotype.

In one embodiment, the present invention is directed to an antibody, or antigen-binding fragment thereof, having the antigen binding regions of antibody D5. In one embodiment, the invention provides an antibody, or antigen-binding fragment thereof, comprising a heavy chain variable domain sequence as set forth in SEQ ID NO: 37, and a light chain variable domain sequence as set forth in SEQ ID NO: 38. In one embodiment, the invention is directed to an antibody having a heavy chain variable domain comprising the CDRs of SEQ ID NO: 37, and a light chain variable domain comprising the CDRs of SEQ ID NO: 38. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 37, and comprises a light chain variable region having an amino acid sequence that is at least 95% identical, at least 96% identical, at least 97% identical, at least 98% identical, or at least 99% identical to the sequence set forth in SEQ ID NO. 38. The antibody may further be an IgG1 or an IgG4 isotype.

In one embodiment, the present invention is directed to an antibody, or antigen-binding fragment thereof, having the antigen binding regions of antibody E7. In one embodiment, the invention provides an antibody, or antigen-binding fragment thereof, comprising a heavy chain variable domain sequence as set forth in SEQ ID NO: 39, and a light chain variable domain sequence as set forth in SEQ ID NO: 40. In one embodiment, the invention is directed to an antibody having a heavy chain variable domain comprising the CDRs of SEQ ID NO: 39, and a light chain variable domain comprising the CDRs of SEQ ID NO: 40. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 39, and comprises a light chain variable region having an amino acid sequence that is at least 95% identical, at least 96% identical, at least 97% identical, at least 98% identical, or at least 99% identical to the sequence set forth in SEQ ID NO. 40. The antibody may further be an IgG1 or an IgG4 isotype.

In one embodiment, the present invention is directed to an antibody, or antigen-binding fragment thereof, having the antigen binding regions of antibody E8. In one embodiment, the invention provides an antibody, or antigen-binding fragment thereof, comprising a heavy chain variable domain sequence as set forth in SEQ ID NO: 41, and a light chain variable domain sequence as set forth in SEQ ID NO: 42. In one embodiment, the invention is directed to an antibody having a heavy chain variable domain comprising the CDRs of SEQ ID NO: 41, and a light chain variable domain comprising the CDRs of SEQ ID NO: 42. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 41, and comprises a light chain variable region having an amino acid sequence that is at least 95% identical, at least 96% identical, at least 97% identical, at least 98% identical, or at least 99% identical to the sequence set forth in SEQ ID NO. 42. The antibody may further be an IgG1 or an IgG4 isotype.

In one embodiment, the present invention is directed to an antibody, or antigen-binding fragment thereof, having the antigen binding regions of antibody CT1E1. In one embodiment, the invention provides an antibody, or antigen-binding fragment thereof, comprising a heavy chain variable domain sequence as set forth in SEQ ID NO: 43, and a light chain variable domain sequence as set forth in SEQ ID NO: 44. In one embodiment, the invention is directed to an antibody having a heavy chain variable domain comprising the CDRs of SEQ ID NO: 43, and a light chain variable domain comprising the CDRs of SEQ ID NO: 44. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 43, and comprises a light chain variable region having an amino acid sequence that is at least 95% identical, at least 96% identical, at least 97% identical, at least 98% identical, or at least 99% identical to the sequence set forth in SEQ ID NO. 44. The antibody may further be an IgG1 or an IgG4 isotype.

Antigen binding proteins (e.g., antibodies, antibody fragments, antibody derivatives, antibody muteins, and antibody variants) are polypeptides that bind to CTLA4.

Antigen-binding fragments of antigen binding proteins of the invention may be produced by conventional techniques. Examples of such fragments include, but are not limited to, Fab and F(ab')$_2$ fragments.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

In certain embodiments, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, or at least 99% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has a light chain variable domain sequence that is at least 95% identical, at least 96% identical, at least 97% identical, at least 98% identical, or at least 99% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, or at least 99% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSC->CPPC) in the hinge region (Bloom et al., 1997, *Protein Science* 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2). Thus, the invention also includes, in certain embodiments, variable sequences having at least 95% identity to those sequences disclosed herein.

In certain embodiments, an antibody, or antigen-binding fragment thereof, provided herein has a dissociation constant ($K_D$) of $1\times10^{-6}$ M or less; $5\times10^{-7}$ M or less' $1\times10^{-7}$ M or less; $5\times10^{-8}$ M or less; $1\times10^{-8}$ M or less; $5\times10^{-9}$ M or less; or $1\times10^{-9}$ M or less. In one embodiment, the antibody, or antigen-binding fragment thereof, of the invention as a $K_D$ from $1\times10^{-7}$ M to $1\times10^{-10}$ M. In one embodiment, the antibody, or antigen-binding fragment thereof, of the invention as a $K_D$ from $1\times10^{-8}$ M to $1\times10^{-10}$ M.

Those of ordinary skill in the art will appreciate standard methods known for determining the Kd of an antibody, or fragment thereof. For example, in one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)).

According to another embodiment, Kd is measured using a BIACORE™ surface plasmon resonance assay. The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

In particular embodiments, antigen binding proteins of the present invention have a binding affinity ($K_a$) for CTLA4 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from CTLA4. In one embodiment, the antigen binding protein has a $K_{off}$ of $1\times10^{-4}$ to $^{-1}$ or lower. In another embodiment, the $K_{off}$ is $5\times10^{-5}$ to $^{-1}$ or lower. In another embodiment, the $K_{off}$ is substantially the same as an antibody described herein. In another embodiment, the antigen binding protein binds to CTLA4 with substantially the same $K_{off}$ as an antibody described herein.

In another aspect, the present disclosure provides an antigen binding protein, e.g., an anti-CTLA4 antibody or antigen-binding fragment thereof, that inhibits an activity of CTLA4. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein, e.g., an anti-CTLA4 antibody or antigen-binding portion thereof, inhibits an activity of CTLA4 with substantially the same $IC_{50}$ as an antibody described herein. In one embodiment, the activity of CTLA4 that is inhibited by an antibody, or antigen binding fragment thereof, as disclosed herein, is binding of CTLA4 to CD80 and/or CD86. In one embodiment, an anti-CTLA4 antibody, or antigen-binding fragment thereof, of the invention inhibits CTLA4 binding of CD80 with an $IC_{50}$ of $1\times10^{-9}$ or less. In one embodiment, an anti-CTLA4 antibody, or antigen-binding fragment thereof, of the invention inhibits CTLA4 binding of CD80 with an $IC_{50}$ of $5\times10^{-10}$ or less. In one embodiment, an anti-CTLA4 antibody, or antigen-binding fragment thereof, of the invention inhibits CTLA4 binding of CD80 with an $IC_{50}$ of $1\times10^{-10}$ or less. In one embodiment, an anti-CTLA4 antibody, or antigen-binding fragment thereof, of the invention inhibits CTLA4 binding of CD86 with an $IC_{50}$ of $1\times10^{-9}$ or less. In one embodiment, an anti-CTLA4 antibody, or antigen-binding fragment thereof, of the invention inhibits CTLA4 binding of CD86 with an $IC_{50}$ of $5\times10^{-10}$ or less. In one embodiment, an anti-CTLA4 antibody, or antigen-binding fragment thereof, of the invention inhibits CTLA4 binding of CD86 with an $IC_{50}$ of $1\times10^{-10}$ or less. Examples of assays that can be used to test the ability of an anti-CTLA4 antibody to inhibit CTLA4 binding of CD80 or CD86 are known in the art, and are also described in the Examples provided herein.

In another aspect, the present disclosure provides an antigen binding protein that binds to CTLA4 expressed on the surface of a cell and, when so bound, inhibits CTLA4 signaling activity in the cell without causing a significant reduction in the amount of CTLA4 on the surface of the cell. Any method for determining or estimating the amount of CTLA4 on the surface and/or in the interior of the cell can be used. In other embodiments, binding of the antigen binding protein to the CTLA4-expressing cell causes less than about 75%, 50%, 40%, 30%, 20%, 15%, 10%, 5%, 1%, or 0.1% of the cell-surface CTLA4 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half-life, such as described in WO00/09560, incorporated by reference herein.

The present disclosure further provides multi-specific antigen binding proteins, for example, bispecific antigen binding protein, e.g., antigen binding protein that bind to two different epitopes of CTLA4, or to an epitope of CTLA4 and an epitope of another molecule, via two different antigen binding sites or regions. Moreover, bispecific antigen binding protein as disclosed herein can comprise a CTLA4 binding site from one of the herein-described antibodies and a second CTLA4 binding region from another of the herein-described antibodies, including those described herein by reference to other publications. Alternatively, a bispecific antigen binding protein may comprise an antigen binding site from one of the herein described antibodies and a second antigen binding site from another CTLA4 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses).

Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Oligomers that contain one or more antigen binding proteins may be employed as CTLA4 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CTLA4 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA*

88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a CTLA4 binding fragment of an anti-CTLA4 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-CTLA4 antibody fragment or derivative fused to a leucine zipper peptide are expressed in suitable host cells, and the soluble oligomeric anti-CTLA4 antibody fragments or derivatives that form are recovered from the culture supernatant.

Antigen binding proteins directed against CTLA4 can be used, for example, in assays to detect the presence of CTLA4 polypeptides, either in vitro or in vivo. The antigen binding proteins also may be employed in purifying CTLA4 proteins by immunoaffinity chromatography. Blocking antigen binding proteins can be used in the methods disclosed herein. Such antigen binding proteins that function as CTLA4 antagonists may be employed in treating any CTLA4-induced condition, including but not limited to various cancers.

Antigen binding proteins may be employed in an in vitro procedure, or administered in vivo to inhibit CTLA4-induced biological activity. Disorders caused or exacerbated (directly or indirectly) by the proteolytic activation of CTLA4, examples of which are provided herein, thus may be treated. In one embodiment, the present invention provides a therapeutic method comprising in vivo administration of a CTLA4 blocking antigen binding protein to a mammal in need thereof in an amount effective for reducing a CTLA4-induced biological activity.

In certain embodiments, antigen binding proteins of the invention include fully human monoclonal antibodies that inhibit a biological activity of CTLA4.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CTLA4 bound thereto. Polypeptides contemplated for use herein include substantially homogeneous recombinant mammalian anti-CTLA4 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CTLA4 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system. CTLA4-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis. The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to CTLA4. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O $(CH_2CH_2O)_n$—$CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal.

Therapeutic Methods, Formulations and Modes of Administration

The present disclosure further provides a method for treating a disease requiring either stimulation of immune responses or suppression, comprising administering an anti-CTLA4 polypeptide. Any of the antibodies disclosed herein may be used in such methods. For example, the methods may be performed using an anti-CTLA4 polypeptide is selected from the group consisting of a fully human antibody of an IgG class that binds to a CTLA4 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, including the heavy and light chain variable regions (and CDRs within said sequences) described in SEQ ID Nos. 1-44 (Table 4).

For example, in one embodiment, the methods disclosed herein include the use of a fully human antibody having a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, and SEQ ID NO. 43, and having a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, and SEQ ID NO. 44.

In one embodiment, the methods described herein include the use of a fully human antibody Fab fragment has the heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, and SEQ ID NO. 43, and that has the light chain variable domain sequence that is at least 95% identical, at least 96% identical, at least 97% identical, at least 98% identical, or at least 99% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, and SEQ ID NO. 44.

In one embodiment, the methods described herein include the use of a single chain human antibody comprising a heavy chain variable domain sequence that is at least 95% identical, at least 96% identical, at least 97% identical, at least 98% identical, or at least 99% identical to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, and SEQ ID NO. 43, and comprising a light chain variable domain sequence that is at least 95% identical, at least 96% identical, at least 97% identical, at least 98% identical, or at least 99% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, and SEQ ID NO. 44.

In one embodiment, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, and SEQ ID NO. 43/SEQ ID NO. 44.

In one embodiment, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, and SEQ ID NO. 43/SEQ ID NO. 44.

In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, and SEQ ID NO. 43/SEQ ID NO. 44.

In one embodiment, the antibodies and antibody fragments of the invention are used to treat a disease is selected from the group consisting of cancers of the prostate, kidney, colon, lung or breast; pathogenic infections; diseases associated with the CNS, amyloidogenic Alzheimer's disease; and diseases with inflammatory or allergic components, graft versus host disease, host versus graft disease, allergy, autoimmune diseases and other inflammatory diseases.

The antibodies and antigen binding fragments thereof, of the invention may be used to treat diseases such as cancer. In one embodiment, the invention features methods of treating cancer that is a CTLA4-associated cancer. The phrase "CTLA4 associated cancer" refers to a cancer or malignant cell transformation that is associated with aberrant CTLA4 expression or activity, for example, increased CTLA4 expression or activity. Examples of a CTLA4-associated cancer include, but are not limited to, bladder cancer, blood cancer, brain cancer, breast cancer, colorectal cancer, fibrosarcoma, lung cancer, ovarian cancer, prostate cancer, melanoma, lymphoma, mesothelioma, and plasmacytoma (see, for example, Grosso et al., Cancer Immun 2013; 13:5; Postow et al., JCO Jan. 20, 2015, Kvistborg et al., Science Translational Medicine 17 Sep. 2014: Vol. 6, Issue 254, pp. 254; Hersh et al., J Clin Oncol. 2008; 26: abstract 9022). In certain embodiments, a CTLA4 associated cancer is any cancer in an individual where biomarkers that correlate with anti-CTLA-4 clinical activity are detected, for example a rise in absolute lymphocyte counts, sustained inducible T cell costimulator (ICOS) expression on T cells (Liakou et al. Proc Natl Acad Sci USA. 2008; 105:14987-14992) or an upregulation of HLA-DR/CD45RO on T cells (Comin-Anduix B, et al. J Transl Med. 2008; 6:22).

Fully human antibodies to human CTLA4 as disclosed herein can be used in methods of treatment requiring either stimulation of immune responses or suppression. Stimulation is achieved using antibodies that block binding of human CTLA4 to human B7 and diseases amenable to treatment by stimulation and augmentation of prolonging of immune responses include cancers of the prostate, kidney, colon, lung or breast; pathogenic infections; diseases associated with the CNS e.g. amyloidogenic diseases including Alzheimer's disease; and diseases with inflammatory or allergic components Immunosuppression can also be achieved using antibodies to human CTLA4, for example through induction of regulatory T cells (Coquerelle et al., Gut 2009; 58: 1363-1373). Diseases amenable to treatment include graft versus host disease, host versus graft disease, allergy, autoimmune diseases and other inflammatory diseases.

The anti-CTLA4 antibodies (and fragments thereof) of the disclosure are also useful in the treatment of autoimmune diseases and the rejection of cell, organ or tissue graft transplants. In certain aspects, the anti-CTLA4 antibodies (and fragments thereof) are useful in treating an autoimmune disease selected from rheumatoid arthritis and juvenile idiopathic arthritis.

The present disclosure features method for treating or preventing the *S. aureus* infection comprising administering an anti-CTLA4 polypeptide. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Preferably, in certain embodiments, the disclosed antibodies are administered by inhalation, but aerosolization of full IgG antibodies may prove limiting due to their molecular size (~150 kDa). To maximize available commercial aerosolization devices, smaller Fab fragments may be required. In this case, we may also need to generate Fab fragments from the parental IgG molecules. Therefore, we will perform initial studies using standard enzyme-based digestion methodologies for the generation of Fab fragments, which will then be characterized in parallel with full IgG molecules.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 μg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

A CTLA4 binding polypeptide, as disclosed herein, can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-CTLA4 antibodies agents of the invention can be used alone.

In certain embodiments, the binding polypeptides of fragments thereof can be labeled or unlabeled for diagnostic purposes. Typically, diagnostic assays entail detecting the formation of a complex resulting from the binding of a binding polypeptide to CTLA4. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CTLA4 protein is combined with the subject binding polypeptides, binding occurs between the binding polypeptides and the CTLA4 protein. In one embodiment, a sample containing cells expressing a CTLA4 protein (e.g., endothelial cells) is combined with the subject antibodies, and binding occurs between the binding polypeptides and cells bearing a CTLA4 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a CTLA4 protein in a biological sample can also be prepared. Such kits will include a CTLA4 binding polypeptide which binds to a CTLA4 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

Having now described the present invention in detail, the same will be more clearly understood by reference to the following examples, which are included for purposes of illustration only and are not intended to be limiting of the invention.

Example 1

Human antibodies specific for human CTLA4 were identified and selected for therapeutic characteristics, including specificity for CTLA4 and a high degree of affinity for CTLA4 (e.g., at least $10^{-6}$ M). The identified antibodies are described in Table 4.

Figure 2:
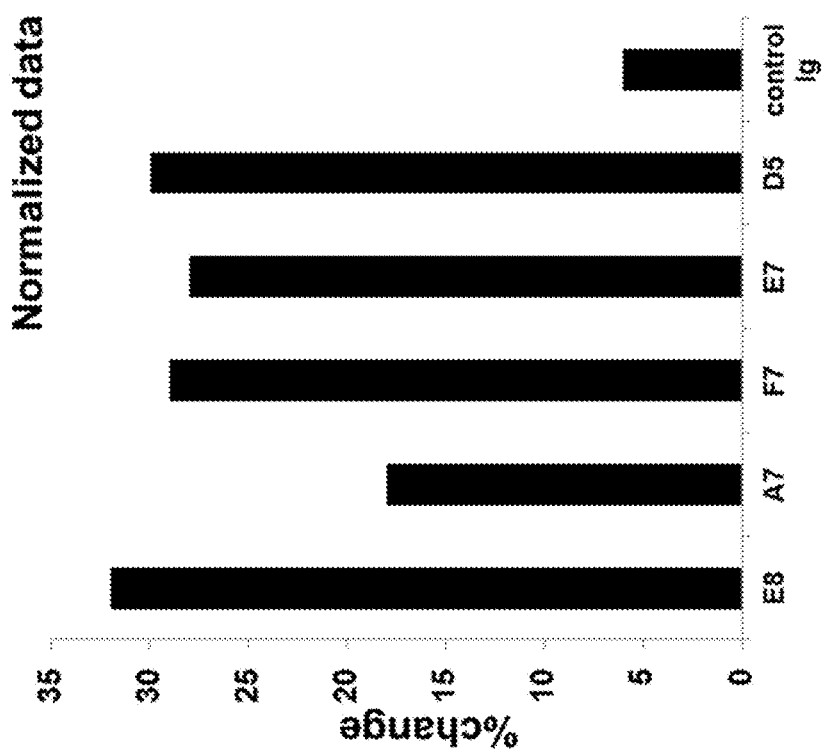
FIG. 2 shows that by normalizing the data with respect to a medium control, a notable level of augmentation was detected in the cultures which received anti-CTLA4 antibodies. The control antibody used (control Ig) is an isotype matched, non-specific (i.e., does not bind CTLA4) antibody.

To determine if the anti-CTLA4 antibodies had functional activity, their ability to augment T cell activation was determined. Peripheral blood mononuclear cells (PBMC) were depleted of monocytes using biotinylated anti-CD14 antibodies followed by reactivity with anti-biotin coated magnetic beads and separated using a magnetic column. The fraction of cells eluted from a column maintained in a magnetic field were collected, yielding a population of lymphocytes that contained <1% monocytes. The lymphocytes were added to wells pre-coated with immobilized anti-CD3 (5 mg/ml). Test antibodies were added to these wells at 10 mg/ml. After three days of culture, the cells were assayed for cell activation by measuring the expression of CD25. Specifically, after three days of culture, the cells were harvested and stained with anti-human CD25 as a measure of cell activation. The level of CD25 expression was higher in the cultures where anti-CTLA4 antibodies had been added (FIG. 1). The control antibody was an isotype matched, nonspecific (i.e., does not bind to CTLA4) antibody. By normalizing the data with respect to the medium control, a notable level of augmentation was detected in the cultures which received anti-CTLA4 antibodies (FIG. 2).

Example 2

This example determines affinity kinetics for an exemplary antibody (F7) disclosed herein. Table 1 shows affinity kinetics for antibody F7.

TABLE 1

Binding characteristics of antibody F7

| mAb | ka (1/Ms) | kd (1/s) | KD (M) | Chi2 |
| --- | --- | --- | --- | --- |
| F7 | 2.94E5 | 2.17E−4 | 7.38E−10 | 0.805 |

This example illustrates binding affinities of exemplary anti-CTLA4 antibodies disclosed herein. Affinities were determined using surface plasmon resonance (Biacore). Briefly, Anti-human Fc antibody (GE, BR-1008-39) was immobilized on CM5 sensor chip to approximately 1000 RU using standard NHS/EDC coupling methodology. Antibodies (about 10 μg/ml) were captured for 60 s at a flow rate 10 μl/min Recombinant human CTLA4/His was serially diluted in running buffer (HBS-EP). All measurements were conducted with a flow rate of 30 μL/min. Surfaces were regenerated with 3M $MgCl_2$ for 60 s. A 1:1 (Langmuir) binding model was used to fit the data.

Example 3

The following example describes the characterization of human anti-CTLA4 antibody CT1E1. The amino acid sequence of the variable heavy and light chains of CT1E1 are provided in SEQ ID Nos: 43 and 44, respectively.

Cross-reactivity studies of anti-CTLA4 antibody CT1E1 revealed that CT1E1 not only was specific to human CTLA4, but cross-reacted with both cynomolgus and murine CTLA4. Using a 96-well Ni-NTA plate recombinant human CTLA4/His, cynomolgus CTLA4/His or mouse CTLA4/His @ 1 μg/mL were captured. The plate was incubated for 30 min at room temperature, washed 3 times with PBS-Tween (PBST), then anti-CTLA4 antibodies (~1 μg/mL) diluted in casein were added and incubated for 30 min with shaking. The plate was washed 3 times with PBST, horseradish peroxidase (HRP)-conjugated goat anti-human Fc (1:500 in casein) was added, then 3,3',5,5'-Tetramethylbenzidine (TMB) was added as substrate and developed about 5 min. 2M $H_2SO_4$ was used to stop the reaction and the OD was read at 450 nm.

The affinity of antibody CT1E1 for human CTLA4 was also determined using surface plasmon resonance (BiaCore). Anti-human Fc antibody (GE, BR-1008-39) was immobilized on CMS sensor chip to approximately 1000 RU using standard NHS/EDC coupling methodology. Antibodies (about 10 μg/ml) were captured for 60 s at a flow rate 10 ul/min Recombinant human PD-L1/His was serially diluted in running buffer (HBS-EP). All measurements were conducted in HBS-EP buffer with a flow rate of 30 μL/min. The antibody was diluted appropriately to obtain a series of concentrations. A 1:1 (Langmuir) binding model was used to fit the data. The Chi2 (chi-squared) value was used as a guideline for fitting quality. Results from the affinity studies are provided below in Table 2.

TABLE 2

| | ka (1/Ms) | kd (1/s) | Rmax (RU) | KD (M) | Chi$^2$ |
|---|---|---|---|---|---|
| | CT1E1 Binding Characteristics | | | | |
| CT1E1 | 1.33E5 | 2.42E-4 | 125.8 | 1.81E-9 | 1.28 |

Assays were performed to determine the ability of antibody CT1E1 to inhibit CD80 and CD86 activity. A 96-well Ni-NTA plate was coated with 1 µg/mL recombinant human CD80 or CD86 with hexahistidine tag at room temperature for 1h. Pre-mixed 30 µL serial 3-fold diluted IgGs (started from 25 µg/mL) and 30 µL of 0.006 µL/mL recombinant human CTLA4 (as human Fc fusion) and incubated the mixtures for 30 minutes, then washed the plate with PBS-Tween (PBST) 3 times. The mixtures were transferred 50 µL to the ELISA plate and incubated 30 min with shaking. The plate was washed 3 times with PBST, then horseradish peroxidase (HRP)-conjugated goat anti-human Fc (1:500 in casein) was added, then 3,3',5,5'-Tetramethylbenzidine (TMB) was added as substrate and developed 30 min. 2M $H_2SO_4$ was used to stop the reaction and the OD was read at 450 nm.

Figure 3A:
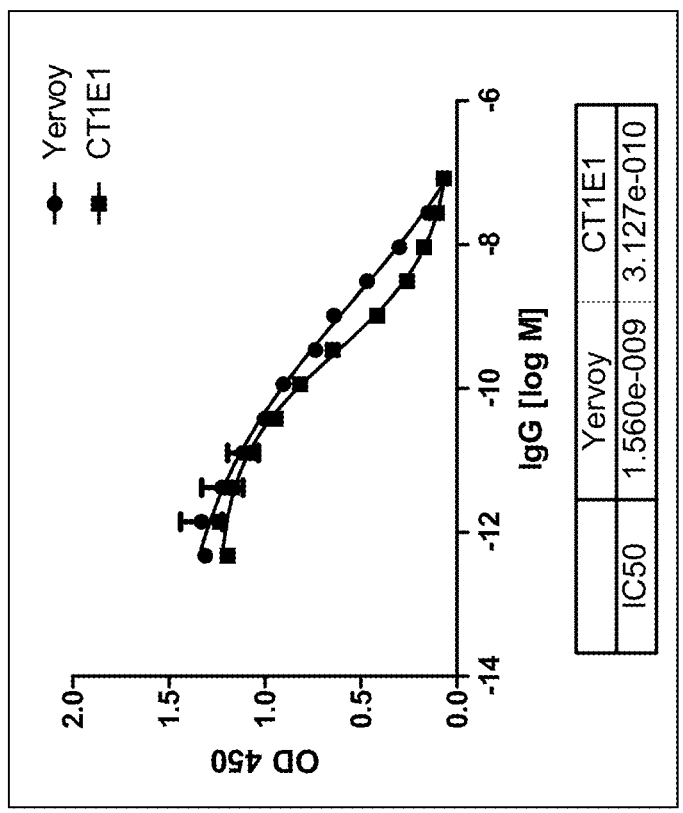
FIGS. 3A and 3B graphically depicts IC50 characteristics of antibody CT1E1 using CD80 (FIG. 3A) and CD86 (FIG. 3B) based assays in comparison to anti-CTLA4 antibody ipilimumab (Yervoy).
Figure 3B:
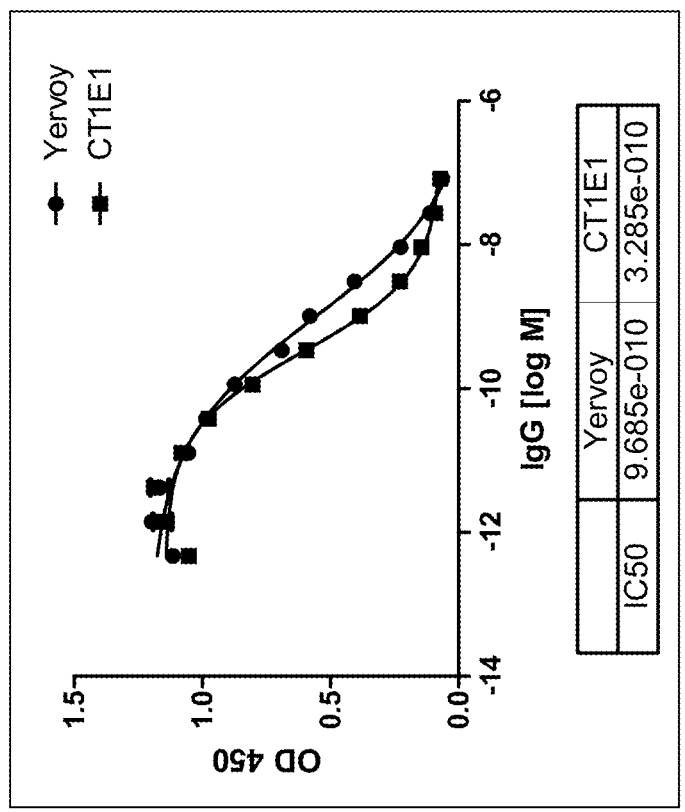

Results from the studies are described in FIGS. 3A (CD80) and 3B (CD86). The IC50 value of CT1E1 for CD80 was determined to be about $0.31 \times 10^{-9}$, and about $0.32 \times 10^{-9}$ for CD86. Surprisingly, antibody CT1E1 has a better IC50 value for CD80 and CD86 versus the calculated IC50 of control antibody ipilimumab (Yervoy), which is a human anti-CTLA4 antibody which is able to inhibit CTLA4 activity such that cytotoxic T cells can, for example, destroy cancer cells. The calculated IC50 values for CD80 and CD86 for both ipilimumab and CT1E1 are described in FIGS. 3A and 3B.

Example 4

This example describes experiments examining the effect of anti-CTLA4 antibody F7 on the response to low dose superantigen *Staphylococcus* enterotoxin B (SEB). The use of SEB as a stimulus provides a means to study T cell activation in response to an antigen. Whereas anti-CD3 is a polyclonal T cell activator, SEB is an oligiclonal activator.

Experiments were performed in which anti-human CD25 was used as a measure of cell activation. Two different concentrations of the F7 antibody were used (30 µg and 10 µg). A negative control was also used, which was an isotype matched antibody that did not bind to CTLA4. After three days, percent activation of CD25 cells was measured.

Figure 4:
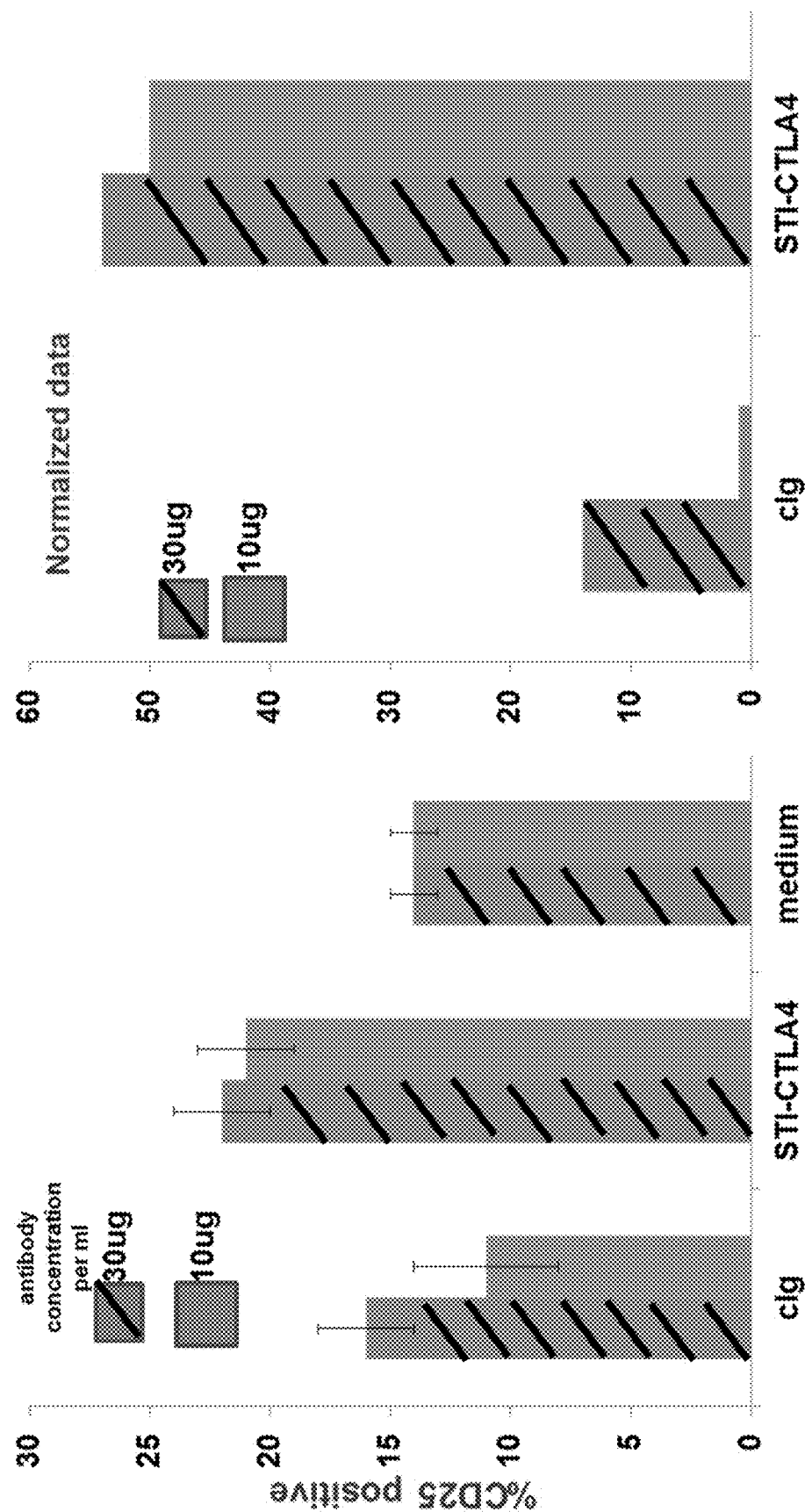
FIG. 4 graphically depicts results from experiments determining the effect of anti-CTLA4 antibody F7 on the response to low dose superantigen *Staphylococcus* enterotoxin B (SEB). The control antibody (cIg) is an isotype matched, non-specific (i.e., does not bind CTLA4) antibody.

As shown in FIG. 4, the percent of activated CD25 cells was increased in cells treated with both concentrations of the anti-CTLA4 F7 antibody (30 µg and 10 µg). By normalizing the data with respect to the medium control, a notable level of activation was detected (by way of CD25 cells) in the cultures which received the F7 anti-CTLA4 antibody (FIG. 4).

Example 5

Antibody E8 was further studied in additional affinity and functional studies. The affinity of antibody E8 for human CTLA4 was determined using surface plasmon resonance (BiaCore). The results of the study are provided below in Table 3.

TABLE 3

| | | Biacore study of antibody E8 | | | |
|---|---|---|---|---|---|
| name | ka (1/Ms) | kd (1/s) | KD (M) | Rmax (RU) | Chi2 |
| E8 | 8.29E4 | 4.88E-3 | 5.89E-8 | 85 | 0.8 |

Figure 5:
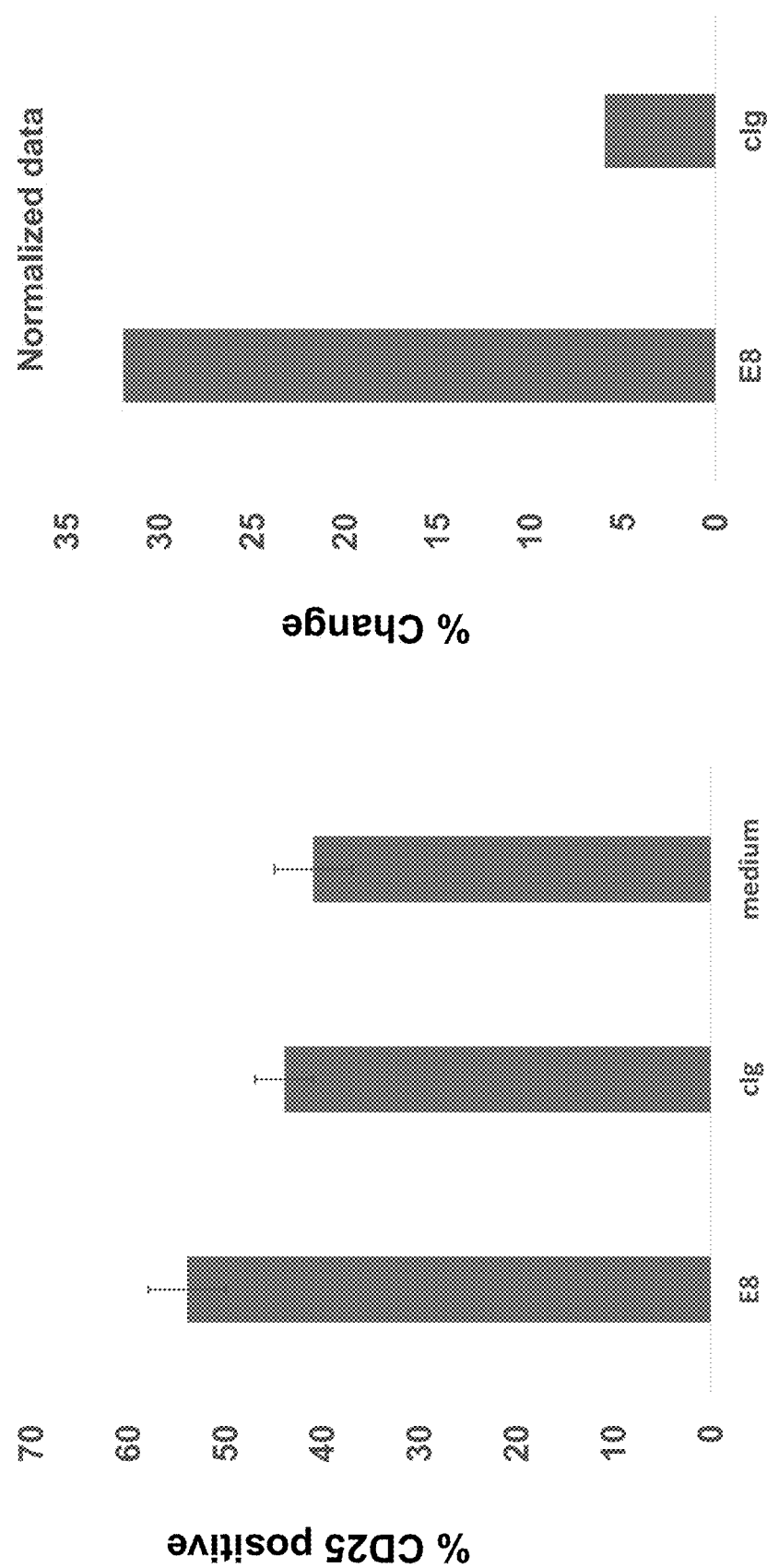
FIG. 5 shows functional activity of anti-CTLA4 antibody E8 and its ability to augment T cell activation. The level of CD25 expression was higher in the cultures where E8 had been added. The control antibody used (control Ig) is an isotype matched, non-specific (i.e., does not bind CTLA4) antibody. Normalized data is on the right.

In addition to affinity studies, FIG. 5 provides results showing the functional activity of antibody E8. The functional assay described in FIG. 5 is similar to the methods used in the CD26 assay of Example 1.

TABLE 4

| | Heavy and Light Chain Variable Domain Amino Acid Sequences | |
|---|---|---|
| | Heavy chain variable domain region | Light chain variable domain region |
| A1 | EVQLVQSGGGLVQPGRSLRLSCRGSNFNF DDLAISWVRQAPGKGLEWLGFVRSKAYG ETTDYVASVKGRFTISRDDSKFIAWLQMD SLKTDDTAVYYCTTFNYWGQGTLVTVSS SEQ ID NO. 1 | LPVLTQPPSVSVAPGKTARISCGGN NIASEAVHWYQKKPGQAPVLVIYY DSDRPSGIPERFSGSNSGNTATLRISR VDAGDEADYYCQVWDRTTDQPVF GGGTKLTVL SEQ ID NO. 2 |
| A2 | QMQLVQSGAEVKMPGSSVRISCKASGGSF TTHFINWVRQAPGQGLEWMGWMNPNTG NTGYAERFQGRVTLTRDTSISTAYLELSSL RSDDTAVYYCARNPAESGRFDPWGQGTL VTVSS SEQ ID NO. 3 | QSALTQPPSASGSPGRSVTISCTGTS NNVGGYNYVSWYQQHPGKAPKLM IYEVTKRPSGVPDRFSGSKSGNTASL TVSGLQAEDEADYYCGTWDGSLNA YVFGTGTKVTVL SEQ ID NO. 4 |
| A4 | QVQLVESGGGLIQPGGSLRLSCAASGFSVS NNYMNWVRQAPGKGLEWVSVIYRGGST YYADSVKGRFTISRDNSKNTLYLQMNSLR TEDTAVYYCLREGGTSGDYVNDWGQGTL VTVSS SEQ ID NO. 5 | QSVVTQPPSVSGAPGQRVTISCTGSS SNIGAGYDVHWYQQLPGTAPKLLIY GNKNRPSGVPDRFSGSKSGTSASLAI TGLQAEDEADYYCQAYDSSLSVVF GGGTKLTVL SEQ ID NO. 6 |
| A7 | QMQLVQSGAEVKKPGASVKVSCKASGGT FSSYAISWVRQAPGQGLEWMGGIIPIFGTA NYAQKFQGRVTITADESTSTAYMELSSLRS EDTAVYYCAREIGSYSSGWYRAFDIWGQG TMVTVSS SEQ ID NO. 7 | DIVMTQSPSTLSASVGDRVTITCRAS QSISSWLAWYQQKPGKAPQLLIYKA SNLQSGVPSRFSGSGSVTEFSLTISSL LPEDFATYYCQQYSRPPWTFGQGT KVEIK SEQ ID NO. 8 |

TABLE 4-continued

Heavy and Light Chain Variable Domain Amino Acid Sequences

| | Heavy chain variable domain region | Light chain variable domain region |
|---|---|---|
| A12 | QVQLVESGGGLVQPGGSLRLSCAASGFTF SNYAMNWVRQTPGKGLEWVSVNYNDGF GTFNGYYADSVKGRFIISRDNSKNTLYLQ MNSLRVDDTAVYYCARDSGVAGPYYFDN WGQGTLVTVSS SEQ ID NO. 9 | AIQLTQSPSTLSASVGDRVTITCRAS QSISSWLAWYQQKPGKAPKLLIYKA SSLESGVPSRFSGSGSGTEFTLTISSL QPDDFATYYCQQYNSSPLTFGGGTK LEIK SEQ ID NO. 10 |
| B6 | QVQLVQSGAEVKKPGATVKVSCTASGFPF RNYAMHWVRQAPGQRLEWLGWIDAGNG NTKYSQTFHGRVTITRDTSASTAYMELSSL RSEDTAVYYCARDLLWPYLVTSGGAFDI WGQGTMVTVSS SEQ ID NO. 11 | SYELMQPPSTSGTPGQRVTISCSGSS SNIGSHIVNWYQQFPGAAPQLLIYN DDQRPSGVPDRFSGSKSGASASLAIS GLQSEDEAHYYCSAWDDILKGPVF GGGTKLTVL SEQ ID NO. 12 |
| C2 | QVQLVQSGAEVKKPGASVKVSCKASGYT FTTHYIHWVRQAPGQGLEWMAIINPNDGV KVYAQKFKGRLTVASDTSATTVYMDLSG LTSDDTAVYYCGREQHGGHHDYWGQGT LVTVSS SEQ ID NO. 13 | QAGLTQPASVSGSPGQSITISCTGTS SDVGGYNYVSWYQQHPGKAPKLMI YDVTNRPSGVSNRFSGSKSGNTASL TISGLQAEDEADYYCKSYTSSSTPY VFGTGTKVTVL SEQ ID NO. 14 |
| D6 | EVQLVQSGGGLVQPGRSLRLSCRGSNFNF DDLAISWVRQAPGKGLEWLGFVRSKAYG ETTDYVASVKGRFTISRDDSKFIAWLQMD SLKTDDTAVYYCTTFNYWGQGTLVTVSS SEQ ID NO. 15 | LPVLTQPPSVSVAPGKTARISCGGN NIASEAVHWYQKKPGQAPVLVIYY DSDRPSGIPERFSGSNSGNTATLRISR VDAGDEADYYCQVWDRTTDQPVF GGGTKLTVL SEQ ID NO. 16 |
| F1 | EVQLVQSGAEVKKPGASVKVSCKASGYTF TSYGISWVRQAPGQGLEWMGWISAYNGN TNYAQKLQGRVTMTTDTSTSTAYMELRSL RSDDTAVYYCARVGYGGYFDYWGQGTL VTVSS SEQ ID NO. 17 | SYELMQPPSVSKGLRQTATLTCTGN SNNVGNQGADWLQQHQGHPPKLLS YRNNDRPSGISERFSASRSGSTASLTI TGLQPEDEADYYCLAWDSSLSAWV FGGGTKVTVL SEQ ID NO. 18 |
| F3 | QMQLVQSGAEVKKPGASVTVSCKASGYT FTNSYIHWVRQAPGQGLEWVGRLIPSSGY TIFSQKLQGRVSMTRDTSMSTHYLTLSHLR PEDTAVYYCATDGGNYNLDFTVGQGTLVT VSS SEQ ID NO. 19 | QPVLTQPPSVSGSPGQSVTISCTGTS SDVGGYNYVSWYQQHPGKAPKLMI YDVSSRPSGVSNRFSGSKSDNTASL TISGLQAEDEADYYCSSYTSSSPYVF GTGTKVTVL SEQ ID NO. 20 |
| F5 | EVQLVQSGTEVKKPGSSVKVSCKASGGSF SNYAISWVRQAPGQGLEWMGRIIPILGIAN YAQKFQGRVTITADKSTSTAYMELSSLGS EDTAVYYCARESGSYLDPWGQGTLVTVSS SEQ ID NO. 21 | DIVMTQSPDSLAVSLGERATINCKSS QSVLYSPNNKNYLTWYQQKPGQPP KLLMYWASTRESGVPDRFSASGSG TDFTLTISSLQAEDVAVYYCQQSRS GPYTFGQGTKVEIK SEQ ID NO. 22 |
| F6 | EVQLVESGGGFVKPGRSLRLSCTASGFTFG DYGMSWFRQAPGKGLEWVGFIRSKAYGG TTDYAASVKGRFTISRDDSKSFAYLQMNS LKTEDTAVYYCTRGHYSASIWGQGTLVTV SS SEQ ID NO. 23 | SYELMQPPSVSVAPGKTARITCGGN NIGSKSVHWYQQRPDQAPVLVIYSD NDRPSGIPERFSGSSSGHTATLTISRV EAGDEADYFCQVWDSNKNEWVFG GGTKLTVL SEQ ID NO. 24 |
| F7 | QVQLVQSGAEVKKPGASVKVSCKASGYA FDGHYMHWVRQAPGQRLEWMGWVDPH SGATNYAQNFQGGVTMTRDTSINTVYME LSSLKSDDTAVYYCARDFYDTSAKSGAFD IWGQGTMVTVSS SEQ ID NO. 25 | AIQLTQSPSSVSASVGDRVTITCRAS QGISSWLAWYQQKPGKAPKLLIYA ASSLQSGVPSRFSGSGSGTDFTLTISS LQPEDFATYYCQQVNSFPWAFGQG TKVEIK SEQ ID NO. 26 |
| G1 | QVQLVQSGAEVKKPGASVKVSCKTSGNTF TNYYMHWVRQAPGQGLEWMGIMNPSGG STSYAQKFQGRVTMTRDKSTSTVYMELSS LTSEDTAVYYCARDLFPHIYGNYYGMDIVV GQGTTVTVSS SEQ ID NO. 27 | QSVVTQPPSVSAAPGQNVTISCSGSS SNIGNNYVSWYQQLPGTAPKLLIYD NNRRASGIPDRFSGSKSGTSATLGIT GLQTGSEDEADYYCGTWDRSLTTDW VFGGGTKLTVL SEQ ID NO. 28 |
| G2 | QVQLVESGGGLIQPGGSLRLSCAASGFTVS SAYMSWVRQAPGKGLEWVSVIYRGGTTY YADSVKGRFTISRDNSKNTLYLQMNSLRA EDTAVYYCRGEGGNSGDYFDYWGQGTTV TVSS SEQ ID NO. 29 | NFMLTQPASVSGSPGQSITISCTGTS SDVGGYNFVSWYQQHPGKAPKLMI YDVSKRPSGVSNRFSGSKSGNTASL TISGLQAEDEADYYCSSYTSTNTLD VLFGGGTKLTVL SEQ ID NO. 30 |
| G3 | QVQLVQSGAEVKKPGASVKVSCKASGYT FTSYYMHWVRQAPGQGLEWMGIINPSGG STSYAQKFQGRVTMTRDTSTSTVYMELSG LRSEDTAVYYCARYEHDYDSSKATTGYFD YWGQGTLVTVSS SEQ ID NO. 31 | AIQLTQSPDSLAVSLGERATINCKSS QSILYRSNNKNYLAWYQQKPGQPP KLLIYWASTRESGVPDRFSGSGSGT DFTLTISSLQPEDFATYYCQQADRFP ITFGQGTRLEIK SEQ ID NO. 32 |
| G5 | QVQLQQSGPGLVKPSQTLSLTCAISGDSVS SNSAAWNWIRQSPSRGLEWLGRTYYRSK WYNDYAVSVKSRITINPDTSKNQFSLQLNS | QSVVTQPPSVSAASGQKVIISCSGSN SNIVNNYVSWYQQLPGAAPKVLIY ANNKRPSGIPDRFSGSKSGTSAFLAI |

TABLE 4-continued

Heavy and Light Chain Variable Domain Amino Acid Sequences

| | Heavy chain variable domain region | Light chain variable domain region |
|---|---|---|
| | VTPEDTAVYYCARDRWELPFDYWGQGTT VTVSS SEQ ID NO. 33 | TGLQTGDEADYYCGTWDGSLDVD VFGGGTKLTVL SEQ ID NO. 34 |
| G12 | EVQLVESGAEVKKPGASVKVSCKASGYTF TSYGISWVRQAPGQGLEWMGWISAYNGN TNYAQKLQGRVTMTTDTSTSTAYMELRSL RSDDTAVYYCARGPGILTGYYFDYWGQG TLVTVSS SEQ ID NO. 35 | EIVMTQSPSSLSASVGDRVTITCRAS QGINYHLAWYQQKPGKAPKLLIYA ASALQSGVPSRFSGTGSGTEFTLTIS SLQPEDFATYYCQQFNTYPLTFGGG TKLEIK SEQ ID NO. 36 |
| D5 | QVQLQQSGPGLVKPSQTLSLTCAISGDSVS SNSAAWNWIRQSPSRGLEWLGRTYYRSK WYNDYAVSVKSRITINPDTSKNQFSLQLNS VTPEDTAVYYCAMHSGYRNYGMDVWGQ GTTVTVSS SEQ ID NO. 37 | QSVVTQPPSVSGAPGQRVTISCTGSS SNIGAGYDVHWYQQLPGTAPKLLIY GNSNRPSGVPDRFSGSKSGTSASLAI TGLQAEDEADYYCQSYDSSLSGAV VFGGGTKLTVL SEQ ID NO. 38 |
| E7 | QVQLVQSGAEVKKPGATVKVSCTASGFPF RNYAMHWVRQAPGQRLEWLGWIDAGNG NTKYSQTFHGRVTITRDTSASTAYMELSSL RSEDTAVYYCARDLLWPYLVTSGGAFDI WGQGTMVTVSS SEQ ID NO. 39 | SYELMQPPSTSGTPGQRVTISCSGSS SNIGSHIVNWYQQFPGAAPQLLIYND DQRPSGVPDRFSGSKSGASASLAISG LQSEDEAHYYCSAWDDILKGPVFG GGTKVTVL SEQ ID NO. 40 |
| E8 | QVQLVQSGAEVKKPGASVKVSCEASGYTF TNYYIHWLRQAPGQGLEWMGIINPSGGST TYAQKFQGRITMTRDTSTNTLYMELSSLR SEDTAIYYCARRDCRGPSCYFAYWGQGTT VTVSS SEQ ID NO. 41 | DIVMTQSPSSLSASVGDRVTITCRAS QSISSYLNWYQQKPGKAPKLLIYAA SSLQSGVPPRFSGSGSGTEFTLTISSL QPEDFATYYCQQANSFPPTFGQGTK VDIK SEQ ID NO. 42 |
| CT1E1 | EVQLVESGGGLVQPGRSLRLSCRGSNFNF DDLAISWVRQAPGKGLEWLGFVRSKAYG ETTDYVASVKGRFTISRDDSKFIAWLQMD SLKTDDTAVYYCTTFNYWGQGTLVTVSS SEQ ID NO: 43 | QPVLTQPPSVSVAPGKTARISCGGN NIASEAVHWYQKKPGQAPVLVIYY DSDRPSGIPERFSGSNSGNTATLRISR VDAGDEADYYCQVWDRTTDQPVF GGGTKLTVL SEQ ID NO: 44 |

We claim:

1. An isolated fully human anti-CTLA4 antibody of an IgG class comprising a heavy chain variable domain comprising an amino acid sequence of SEQ ID NO: 41; and a light chain variable domain comprising an amino acid sequence of SEQ ID NO. 42.

2. The fully human antibody of claim 1, wherein the antibody has a heavy chain/light chain variable domain sequence of SEQ ID NO. 41/SEQ ID NO. 42 (called E8 herein).

3. An anti-CTLA4 fully human antibody fragment comprising a heavy chain variable domain comprising an amino acid sequence of SEQ ID NO: 41; and a light chain variable domain comprising an amino acid sequence of SEQ ID NO. 42, wherein the fragment is a Fab fragment or a single chain antibody comprising a heavy chain variable domain and a light chain variable domain which are connected by a peptide linker.

4. The fully human antibody fragment of claim 3, wherein the antibody fragment has a heavy chain/light chain variable domain sequence of SEQ ID NO. 41/SEQ ID NO. 42.

5. A method of treating cancer or another disease requiring stimulation of an immune response in a subject in need thereof, the method comprising administering an effective amount of the antibody of claim 1, such that the cancer or other disease is treated.

6. The method of claim 5, wherein the cancer is selected from the group consisting of bladder cancer, blood cancer, brain cancer, breast cancer, colon cancer, fibrosarcoma, lung cancer, ovarian cancer, prostate cancer, melanoma, lymphoma, mesothelioma, and plasmacytoma.

7. The method of claim 5, wherein the antibody has a heavy chain/light chain variable domain sequence selected from the group consisting of SEQ ID NO. 41/SEQ ID NO. 42.

8. The method of claim 5, wherein the cancer or another disease is selected from the group consisting of cancers of the prostate, kidney, colon, lung or breast, and pathogenic infections.

* * * * *